(12) United States Patent
Amini et al.

(10) Patent No.: US 12,391,577 B2
(45) Date of Patent: Aug. 19, 2025

(54) THIN FILM COATING

(71) Applicant: MDC GLOBAL TOPCO LIMITED

(72) Inventors: Shahram Amini, Wayne, PA (US); Jeffrey D. Hettinger, Glassboro, NJ (US); Gregory Taylor, Glassboro, NJ (US)

(73) Assignee: MDC GLOBAL TOPCO LIMITED, London (GB)

( * ) Notice: Subject to any disclaimer, the term of this patent is extended or adjusted under 35 U.S.C. 154(b) by 728 days.

(21) Appl. No.: 17/594,232

(22) PCT Filed: May 29, 2020

(86) PCT No.: PCT/GB2020/051300
§ 371 (c)(1),
(2) Date: Oct. 7, 2021

(87) PCT Pub. No.: WO2020/240193
PCT Pub. Date: Dec. 3, 2020

(65) Prior Publication Data
US 2022/0144665 A1 May 12, 2022

Related U.S. Application Data

(60) Provisional application No. 62/855,450, filed on May 31, 2019.

(51) Int. Cl.
| | |
|---|---|
| *C01G 55/00* | (2006.01) |
| *A61B 5/263* | (2021.01) |
| *A61N 1/05* | (2006.01) |
| *C23C 14/00* | (2006.01) |
| *C23C 14/02* | (2006.01) |

(Continued)

(52) U.S. Cl.
CPC ........... *C01G 55/004* (2013.01); *A61B 5/263* (2021.01); *A61N 1/05* (2013.01); *C23C 14/0036* (2013.01); *C23C 14/022* (2013.01); *C23C 14/08* (2013.01); *C23C 14/3464* (2013.01); *C23C 14/3485* (2013.01); *C23C 14/548* (2013.01); *C01P 2002/50* (2013.01); *C01P 2002/60* (2013.01); *C01P 2002/72* (2013.01); *C01P 2004/03* (2013.01); *C01P 2006/40* (2013.01)

(58) Field of Classification Search
None
See application file for complete search history.

(56) References Cited

U.S. PATENT DOCUMENTS 5,181,526 A * 1/1993 Yamasaki ................ A61N 1/05
607/121
5,683,443 A * 11/1997 Munshi ..................... A61N 1/05
607/121

(Continued)

OTHER PUBLICATIONS

Auge et al., "Platinum-group element oxides from the Pirogues ophiolitic mineralization," Economic Geology, vol. 89, 1994, pp. 1454-1468. (Year: 1994).*

(Continued)

*Primary Examiner* — David Sample
(74) *Attorney, Agent, or Firm* — BakerHostetler

(57) ABSTRACT

The present invention provides a thin film coating comprising a metal oxide material, wherein the metal oxide material comprises Ir and metals M and M', wherein M and M' are the same or different and are Ru, Rh, Pd, Os or Pt.

14 Claims, 20 Drawing Sheets

(51) Int. Cl.
*C23C 14/08* (2006.01)
*C23C 14/34* (2006.01)
*C23C 14/54* (2006.01)

(56) References Cited

U.S. PATENT DOCUMENTS

| | | | |
|---|---|---|---|
| 2005/0131509 A1* | 6/2005 | Atanassoska | A61N 1/0565 607/122 |
| 2010/0137963 A1* | 6/2010 | Nygren | A61N 1/05 29/874 |
| 2012/0029585 A1 | 2/2012 | Pickett | |
| 2013/0300254 A1* | 11/2013 | Fujii | H10N 30/875 29/25.35 |
| 2014/0326482 A1 | 11/2014 | Thanawala et al. | |

OTHER PUBLICATIONS

Seley, David et al.m "Combinatorial Search for Improved Metal Oxide Oxygen Evolution Electrocatalysts in Acidic Electrolytes", ACS Combinatorial Science, vol. 15, No. 2, Jan. 22, 2013 (Jan. 22, 2013), pp. 82-89, XP055721045, US, ISSN: 2156-8952, DOI: 10.1021/co300086h; Experimental Section; p. 83-86; Tables 1, 2.

R Kotz, et al., "Stabilization of RuO 2 by IrO 2 for anodic oxygen evolution in acid media", Electrochimica Acta, Jan. 1, 1986 (Jan. 1, 1986), pp. 1311-1316, XP055567532, DOI: 10.1016/0013-4686(86)80153-0; Retrieved from the Internet: URL: https://ac.els-cdn.com/0013468686801530/1-s2.0-0013468686801530-main.pdf?_tid=c40771a5-e2cb-449d-b6bd-fe3e3e85a74e&acdnat=1552379935 47bf07146647da93253ad0548f7e6a9e Abstract and section "Experimental"; p. 1311-p. 1312.

Jaworski R K, et al., "Characterization of oxide films electrochemically deposited from solutions of palladium chloride and sodium hexachloroiridate", Journal of Electroanalytical Chemistry and Interfacial Electrochemistry, Elsevier, Amsterdam, NL, vol. 325, No. 1-2, Mar. 23, 1992 (Mar. 23, 1992), pp. 111-123, XP026518002, ISSN: 0022-0728, DOI: 10.1016/0022-0728(92)80105-D [retrieved on Mar. 23, 1992] Abstract; p. 114.

Kato K, et al., "Preparation of RHO2 Thin Films by Reactive Sputtering and Their Characterizatons", Japanese Journal of Applied Physics, Japan Society of Applied Physics, JP, vol. 40, No. 4A, Part 01, Apr. 1, 2001 (Apr. 1, 2001), pp. 2399-2402, XP001081055, ISSN: 0021-4922, DOI: 10.1143/JJAP.40.2399 the whole document.

R. Vedula, et al., "New electrode-barrier structures for high density ferroelectric memories:", Applied Physics A Materials Science & Processing, vol. 72, No. 1,Jan. 1, 2001 (Jan. 1, 2001), pp. 13-20, XP055721049, Berlin/HeidelbergISSN: 0947-8396, DOI:10.1007/s003390000624Pt-Ir based electrode barriers.; p. 14.

English Translation of Rejection Decision issued in Chinese Patent Application No. 202080029839.1, dated Jan. 11, 2023.

Xiaohong, et al., "New Development of Tissue Engineering and Central Nervous System", p. 115, 2018.

"Biomedical Micro-Nano Electronic Technology", p. 349-350, Mar. 2019.

Casella, et al., Anodic electrodeposition of iridium oxide particles on glassy carbon surfaces and their electrochemical/SEM/XPS characterization, Journal of Electroanalytical Chemistry, 736 (2015) 147-152.

Chen, et al., Free-standing iridium oxide nanotube array for neural interface electrode applications, Materials Letters, 221 (2018) 293-295.

Cho, et al., Preparation and characterization of iridium oxide thin films grown by DC reactive sputtering, Jpn J Appl Phys 1, 36 (1997) 1722-1727.

Cogan, Stuart F., "Neural Stimulation and Recording Electrodes." Annual Review of Biomedical Engineering, vol. 10, No. 1, 2008, pp. 275-309.

Harris, et al., Effective Area and Charge Density of Iridium Oxide Neural Electrodes, Electrochimica Acta, 230 (2017) 285-292.

Kang et al., "Fabrication and Electrochemical Comparison of SIROF-AIROF-EIROF Microelectrodes for Neural Interfaces." 2014 36th Annual International Conference of the IEEE Engineering in Medicine and Biology Society, 2014.

Negi, et al., Effect of sputtering pressure on pulsed-DC sputtered iridium oxide films, Sensors and Actuators B: Chemical, 137 (2009) 370-378.

Thanawala, et al., Characterization of iridium oxide thin films deposited by pulsed-direct-current reactive sputtering, Thin Solid Films, 515 (2007) 7059-7065.

* cited by examiner $$A_R = \frac{d_{min}}{d_{max}}$$

$$A_R = \frac{d_{min}}{d_{max}}$$

THIN FILM COATING

FIELD OF THE INVENTION

The present invention provides a thin film coating comprising a metal oxide material, as well as a method for preparing the thin film coating. The thin film coating has specific use in electrodes in medical devices, such as neurostimulators.

BACKGROUND OF THE INVENTION

As medical device manufacturers are pressed to design ever-smaller devices with increasingly long service life, optimizing the performance and profile of each component becomes more crucial. During the past few decades, various medical devices, for instance cardiac rhythm management and neurostimulation devices have been invented and used in clinical practice to achieve artificial stimulation. These devices function via artificial stimulation of living tissue by transfer of an external electrical signal to an implantable electro-conductive electrode, which transfers the signal to the membrane of the neural cells or tissue. Application examples include pain management, cardiac pacing, suppression of involuntary movements for those with neurological disorders, and for the treatment of seizures. Furthermore, electrodes connecting brain and machine have demonstrated significant promise with the potential for partial restoration of motor skills for those who have lost this function through loss of limb or spinal cord injury. Since 2002, tens of thousands of people have had neurostimulation electrodes implanted for deep brain stimulation and many others have had implanted electrodes for sensory feedback.

In all applications of implantable electrodes, improving the coupling of electrical charge (and electric field) between the biological system and the underlying electrode is extremely important so that electrodes are effective and can be miniaturized to eliminate problems associated with size (scar tissue, increased trauma, longer healing times, and system rejection). Films are aimed at the improvement of the charge coupling, and therefore, the information exchange between the biological fluid and the electrode are currently being developed.

Several films for neurostimulation, cardiac pacing, and diagnostic applications have been synthesized with some using reactive sputtering including the deposition of titanium in a nitrogen-rich atmosphere to form titanium nitride films with large surface areas. Iridium, sputtered in an oxygen-rich atmosphere, has been shown to result in $IrO_2$ films that oxidize and reduce to enhance charge exchange between biological ionic solutions and underlying metallic substrate/electrode [1-4]. Sputtered $IrO_2$ films have been prepared which have good electrochemical performance, but which can have surfaces not suitable for use in implantable medical devices [5,6]. Other reported sputtered $IrO_2$ films include industry standard films used in medical devices which have stable surfaces and charge storage capacities of 4 $mC/cm^2$ [7] to 6 $mC/cm^2$ [8]. Unstable films have been avoided in industrial applications by, for example, sputtering pure Ir and activating through voltage cycling.

SUMMARY OF THE INVENTION

There remains a need for thin film coatings with surfaces suitable for use in implantable medical devices, and which have acceptable electrochemical performance.

Accordingly, in a first aspect the present invention provides a thin film coating comprising a metal oxide material, wherein the metal oxide material comprises Ir and metals M and M', wherein M and M' are the same or different and are Ru, Rh, Pd, Os or Pt.

In a second aspect, the present invention provides a thin film coating comprising a metal oxide material, wherein the metal oxide material is $Rh_{a-1}O_a$, wherein a is in the range of and including 2 to 3. The second aspect of the invention also provides a thin film coating comprising a metal oxide material, wherein the metal oxide material is $RuO_b$, wherein b is in the range of and including 2 to 4.

In a third aspect, the present invention provides a thin film coating comprising a metal oxide material, wherein the metal oxide material has the formula $(Ir_{1-x}[MM']_x)_nO_{n+y}$ wherein;
  x is in the range of and including 0.05 to 1;
  n is in the range of and including 1 to 2;
  y is in the range of and including 0 to 3;
  M and M' are the same or different and are Ru, Rh, Pd, Os or Pt;
  wherein when x is 1, M and M' are the same.

In a fourth aspect, the present invention provides a method of depositing a thin film coating according to the first, second, or third aspects of the invention by reactive sputtering wherein the oxygen partial pressure during reactive sputtering is at least 20%.

In a fifth aspect, the present invention provides a thin film coating obtainable by the method of the fourth aspect of the invention.

The present invention also provides an electrode comprising the thin film coating of the first, second, third or fifth aspects of the invention, as well as a medical device comprising the electrode of the invention.

The present invention also provides the use of the thin film coating of the first, second, third or fifth aspects of the invention as an electrode in a medical device. The present invention also provides the use of the electrode of the invention in a medical device.

The thin film coatings of the invention have surface structures suitable for use in implantable medical devices, and have similar or improved electrochemical performance with respect to known $IrO_2$ films, and $IrO_2$ films prepared by the inventors. Therefore, the thin film coatings of the invention allow for the provision of electrodes in implantable medical devices which demonstrate effective coupling of electrical charge (and electric field) between the biological system and the electrode, in turn allowing effective miniaturisation of the implantable electrodes.

DETAILED DESCRIPTION

Figure 1A:
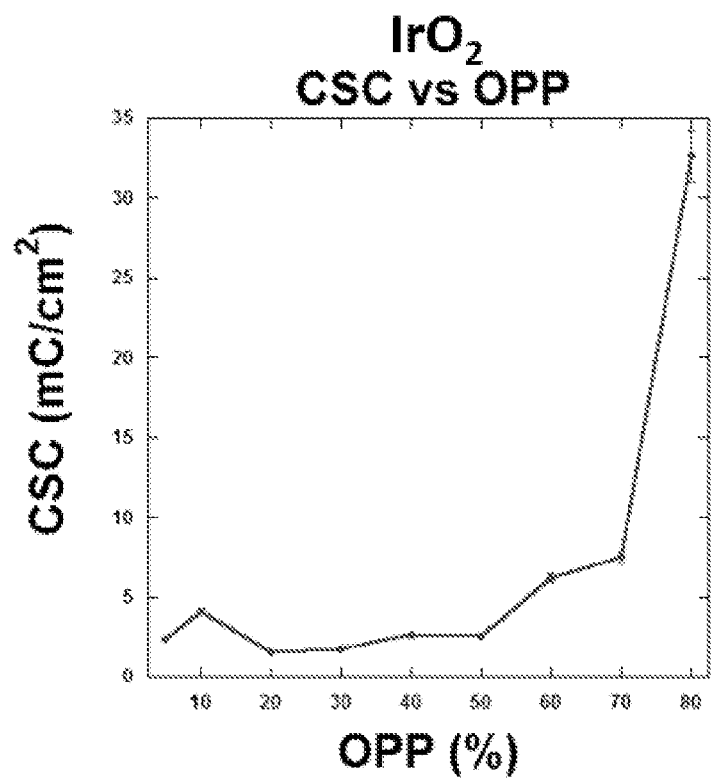
FIG. 1a is a chart showing charge storage capacities for thin films of $IrO_2$ prepared by reactive sputtering at varying oxygen partial pressure.

Preferred and/or optional features of the invention will now be set out. Any aspect of the invention may be combined with any other aspect of the invention unless the context demands otherwise. Any of the preferred and/or optional features of any aspect may be combined, either singly or in combination, with any aspect of the invention unless the context demands otherwise.

Numerical ranges include fractional or decimal values within the range as well as integers. As a non-limiting example, a range of 1 to 2 includes values such as 2.5 and 2.15.

The term "thin film" takes its conventional meaning in the art, which will be understood by a skilled person. Suitably, the thin film coatings of the present invention have a thickness of no more than 5000 nm, typically no more than 2000 nm, suitably no more than 1000 nm, preferably no more than 800 nm, more preferably no more than 500 nm. The thin film coatings typically have a thickness of at least 50 nm, preferably at least 100 nm. Accordingly, the thin films of the invention may have a thickness in the range of and including 100 to 1000 nm, preferably 100 to 800 nm, more preferably 100 to 500 nm.

As will be readily understood, the thin film coatings are coated on a substrate. The identity of the substrate is not particularly limited, provided it can receive a thin film coating according to the invention. Suitable materials when the thin film coating is an electrode (i.e. suitable materials in the electrode of the invention) include NiTi, W, Ta, MP35N nickel alloy, Ti-6Al-4V, Stainless Steel, Pt-10Ir, Pt and Au. A skilled person will be aware of suitable substrates for an electrode. In the case of a medical device comprising the electrode (i.e. suitable materials in the medical device of the invention) suitable materials include any material which is suitable for use in a medical device, preferably a biologically (i.e. in a human) implantable medical device. A skilled person will be aware of suitable substrates for a medical device. For example, the substrate for a medical device, preferably an implantable medical device, may also be NiTi, W, Ta, MP35N nickel alloy, Ti-6Al-4V, Stainless Steel, Pt-10Ir, Pt and Au.

In the first aspect of the invention, thin film coatings comprise a metal oxide material, wherein the metal oxide material comprises Ir and metals M and M', wherein M and M' are the same or different and are Ru, Rh, Pd, Os or Pt. Preferably, the metal oxide material consists essentially of Ir, metals M and M' and oxygen, more preferably, the metal oxide material consist of Ir, metals M and M' and oxygen. The term "consists essentially of" takes its conventional meaning that the materials present other than oxygen, Ir and metals M and M' in the metal oxide material do not materially affect the essential characteristics of the metal oxide material. For example, the metal oxide material comprises at least 90%, preferably at least 95%, more preferably at least 99% by weight of oxygen, Ir and metals M and M'.

When M and M' are the same, this indicates that the metal oxide material contains Ir and a single other metal Ru, Rh, Pd, Os or Pt. In the case that M and M' are different, this indicates that the metal oxide material contains Ir and two different metals selected from Ru, Rh, Pd, Os or Pt. There is no meaning associated with designating a species formally as M or M'.

Preferably, in the first aspect of the invention M and M' are the same or different and are each independently Ru, Rh or Pd. More preferably, M and M' are the same or different and are each independently Ru or Rh. Accordingly, preferable metal oxide materials comprise Ir and metals M and M', wherein M and M' are Rh, or M and M' are Ru, or M is Rh and M' is Ru (equally M is Ru and M' is Rh), or M and M' are Pd.

The atomic ratio of oxygen to total metal species (Ir, M and M') present in the metal oxide material of the first aspect of the invention may be in the range of and including 1:1 to 4:1, suitably 1:1 to 3:1, preferably 1:1 to 2:1, more preferably 3:2 to 2:1. The atomic ratio of Ir to total metal M and M' may be in the range of and including 20:1 to 1:20. Suitably, the atomic ratio of Ir to total metal M and M' is in the range of and including 4:1 to 1:20, typically 3:1 to 1:20, for example 1:1 to 1:20, or 1:2 to 1:20. When M and M' are different, in particular when M is Rh and M' is Ru (or vice versa), the ratio of Ir to total metal M and M' is preferably in the range of and including 3:1 to 1:1, preferably 2:1 to 1:1.

In the preferred metal oxide materials of the first aspect of the invention in which M and M' are Ru, the atomic ratio of oxygen to total metal species Ir and Ru is preferably in the range of and including 4:1 to 2:1, for example the atomic ratio may be 4:1 or 2:1. In the preferred metal oxide materials of the first aspect of the invention in which M and M' are Rh, the atomic ratio of oxygen to total metal species Ir and Rh is preferably in the range of and including 3:2 to 2:1, Accordingly, the atomic ratio can be 3:2 or 2:1, preferably 2:1. When M is Rh and M' is Ru (equally M is Ru and M' is Rh) the atomic ratio of oxygen to total metal species (Ir, M and M') is preferably in the range of and including 4:1 to 2:1, more preferably 3:2 to 2:1. For example, the atomic ratio may be 4:1, 3:2 or 2:1, preferably 3:2 or 2:1, more preferably 2:1. In the preferred metal oxide materials of the first aspect of the invention in which M and M' are Pd, the atomic ratio of oxygen to total metal species Ir and Pd is preferably in the range of and including 3:2 to 2:1. Accordingly, the atomic ratio can be 3:2 or 2:1, preferably 2:1

When M and M' are different, the atomic ratio of M to M' may be in the range of and including 20:1 to 1:20, preferably 5:1 to 1:5, more preferably 1:1 to 1:5. When M is Rh and M' is Ru (or vice versa) the ratio of Rh to Ru is preferably in the range of and including 1:1 to 1:5. When M and M' are the same, it will be appreciated that the ratio of M to M' is not significant.

In a second aspect, the present invention provides a thin film coating comprising a metal oxide material, wherein the metal oxide material is $Rh_{a-1}O_a$, wherein a is in the range of and including 2 to 3. Accordingly, a can be 2 or 3. Also, the second aspect of the invention provides a thin film coating comprising a metal oxide material, wherein the metal oxide material is $RuO_b$, wherein b is in the range of and including 2 to 4. Accordingly, b can be, for example, 2, 3 or 4, preferably 2 or 4.

The third aspect of the invention provides a thin film coating comprising a metal oxide material, wherein the metal oxide material has the formula $(Ir_{1-x}[MM']_x)_nO_{n+y}$ wherein x is in the range of and including 0.05 to 1, n is in the range of and including 1 to 2, and y is in the range of and including 0 to 3; M and M' are the same or different and are Ru, Rh, Pd, Os or Pt; wherein when x is 1, M and M' are the same. Preferably, n+y does not exceed 4. Preferably, x is less than 1.

In the third aspect of the invention, y may be in the range of and including 1 to 3, preferably 1 to 2, more preferably y is 1. Preferably, n is 1. Also, x may be in the range of and including 0.05 to 0.95. Suitably, x may be 0.2 to 0.95, typically 0.25 to 0.95, for example 0.50 to 0.95 or 0.65 to 0.95. Accordingly, x can be, for example, 0.2, 0.25, 0.5 or 0.8. When M and M' are different, x is preferably in the range of and including 0.3 to 0.45.

In the third aspect of the invention when x is 1, the metal oxide material has the formula $(MM')_nO_{n+y}$. In this case, M and M' are preferably Ru or Rh. When M and M' are Ru, i.e. the metal oxide material has the formula $Ru_nO_{n+y}$, n is preferably 1 and y is in the range of and including 1 to 3. Accordingly, y can be 1 or 3. When M and M' are Rh, i.e. the metal oxide material has the formula $Rh_nO_{n+y}$, n is in the range of and including 1 to 2 and y is preferably 1. Accordingly, n can be, for example, 1 or 2 and y is preferably 1.

In the third aspect of the invention when x is less than 1, M and M' are the same or different and are preferably independently Ru, Rh or Pd. More preferably, M and M' are the same or different and are independently Ru or Rh. Accordingly, preferable metal oxide materials of the third aspect of the invention comprise Ir and metals M and M', wherein M and M' are Rh, i.e. the metal oxide material is $(Ir_{1-x}Rh_x)_nO_{n+y}$, or M and M' are Ru, i.e. the metal oxide material is $(Ir_{1-x}Ru_x)_nO_{n+y}$, or M is Rh and M' is Ru (equally M is Ru and M' is Rh), i.e. the metal oxide material is $(Ir_{1-x}[RhRu]_x)_nO_{n+y}$, or M and M' are Pd, i.e. the metal oxide material is $(Ir_{1-x}Pd_x)_nO_{n+y}$.

In the preferred metal oxide materials of the third aspect of the invention in which x is less than 1 and M and M' are Ru, n is preferably 1 and y is in the range of and including 1 to 3. Accordingly, y can be 1, 2 or 3, preferably 1 or 3. In the preferred metal oxide materials of the third aspect of the invention in which x is less than 1 and M and M' are Rh, n is in the range of and including 1 to 2 and y is preferably 1. Accordingly, n can be, for example, 1 or 2, preferably 1 and y is preferably 1. When M is Rh and M' is Ru (equally M is Ru and M' is Rh), n is in the range of and including 1 to 2. Accordingly, n can be 1 or 2, and y is preferably in the range of and including 1 to 3, more preferably 1 to 2. Also, n+y preferably does not exceed 4. Accordingly, for example, n is 1 and y is 3, n is 2 and y is 1, or n is 1 and y is 1, preferably, n is 1 and y is 1. In the preferred metal oxide materials of the third aspect of the invention in which x is less than 1 and M and M' are Pd, n is in the range of and including 1 to 2 and y is preferably 1. Accordingly, n can be, for example, 1 or 2, preferably 1 and y is preferably 1.

When M and M' are different, M is Rh and M' is Ru, the metal oxide material $(Ir_{1-x}[MM']_x)_nO_{n+y}$ may preferably be described as $(Ir_eRh_fRu_g)_{1+m}O_{1+p}$ wherein e+f+g=1, m is in the range of and including 0 to 1, p is in the range of and including 1 to 4, preferably 1 to 2, e is in the range of and including 0.40 to 0.80, preferably 0.55 to 0.70, f is in the range of and including 0.10 to 0.50, preferably 0.20 to 0.40 and g is in the range of and including 0.01 to 0.30, preferably 0.05 to 0.20, more preferably 0.08 to 0.20, m is preferably 0 or 1, and p is preferably 1 or 2. More preferably, m is 0 and p is 1.

The thin film coatings of the first, second, third and fifth aspects of the invention may have a charge storage capacity (CSC) of at least 5 mC/cm$^2$, typically at least 10 mC/cm$^2$, preferably at least 15 mC/cm$^2$, more preferably at least 25 mC/cm$^2$. The maximum charge storage capacity is not particularly limited. For example, the thin film coating may have a charge storage capacity of no more than 200 mC/cm$^2$, typically no more than 150 mC/cm$^2$. It is within the capability of a skilled person to measure charge storage capacity, which is a routine parameter in the art. Charge storage capacity is evaluated by cyclic voltammetry measurements using a phosphate-buffered saline solution, a Pt wire counter electrode and an Ag/AgCl reference electrode. The voltage is swept between the potentials −0.6 to 0.8V at a scan rate of 0.1 Vs. For avoidance of doubt, a detailed method of measuring charge storage capacity is provided in the examples section. For avoidance of doubt, the quoted values refer to the sum total of anodic and cathodic charge storage capacity.

Figure 9:
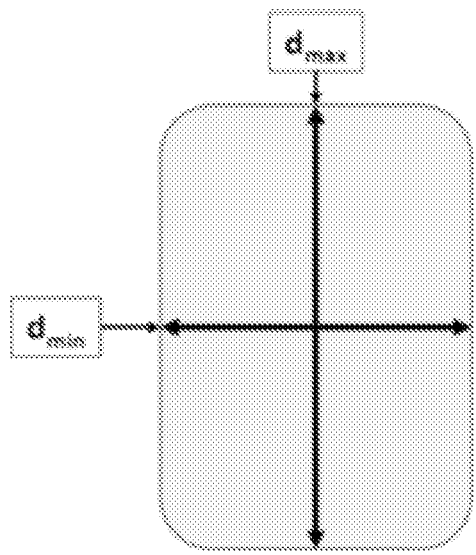
FIG. 9 illustrates how aspect ratio is the ratio of the length of the minor axis to the length of an orthogonal major axis, and equiaxed grains would approach an aspect ratio of 1.

The surface of the thin film coatings of the first, second, third and fifth aspects of the invention consist of grains which suitably have an average aspect ratio in the range of and including 0.05 to 1, preferably 0.25 to 1, more preferably 0.50 to 1, most preferably 0.75 to 1. Also, the surface of the thin film coatings of the first, second, third and fifth aspects of the invention consist of grains which suitably have an average circularity in the range of and including 0.15 to 1, preferably 0.25 to 1, more preferably 0.50 to 1, most preferably 0.75 to 1. Accordingly, the surfaces preferably do not have the unstable nanoflake (or "platelet") structure characteristic of the surface of high CSC IrO$_2$ films such as those shown in the accompanying figures. Aspect ratio is the ratio of the length of the minor axis to the length of an orthogonal major axis. As illustrated in FIG. 9, equiaxed grains would approach an aspect ratio of 1:

Circularity is a measure of how close an object is to being a true circle, which is a function of perimeter (P) and area (A). A spherical grain would have a circularity factor approaching 1 (P=2πr; A=πr$^2$):

$$F_C = \frac{4\pi A}{P^2}$$

Figure 6A:
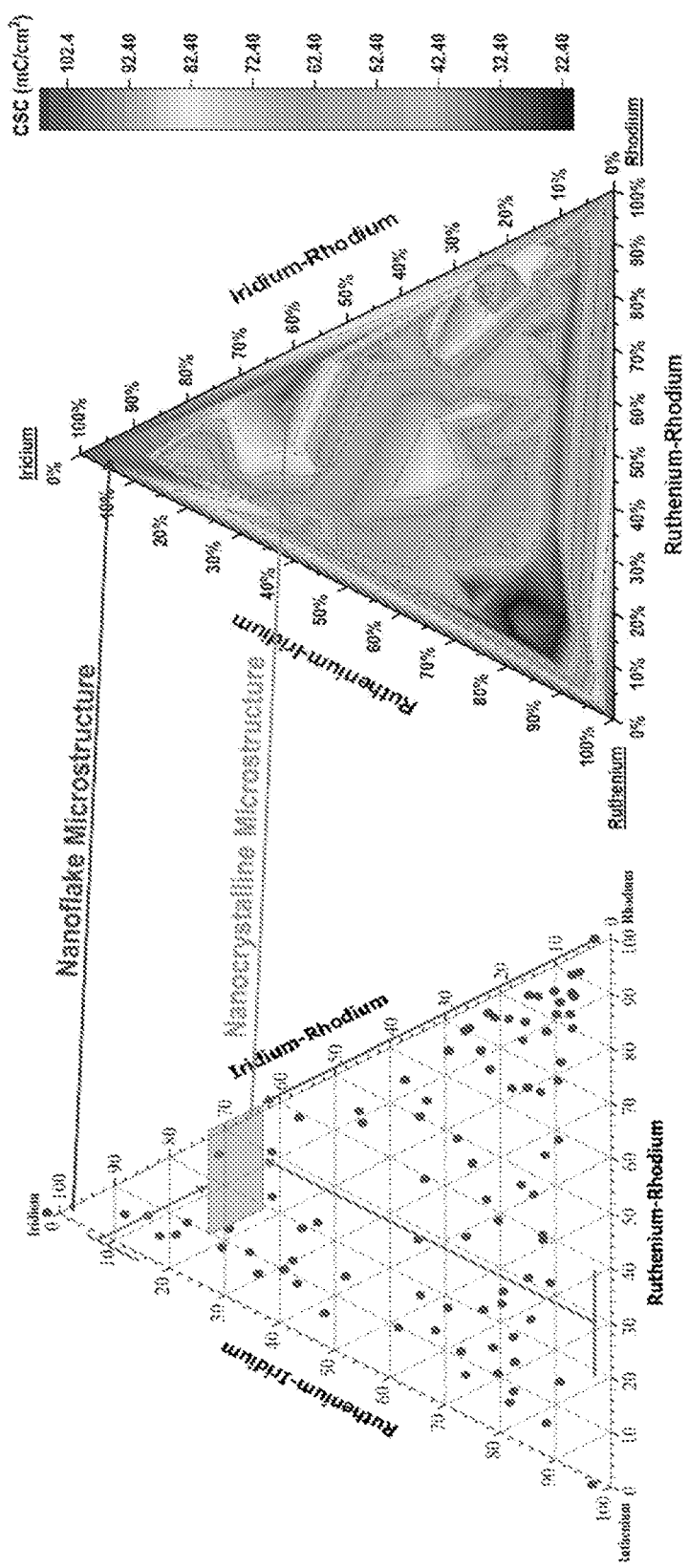
FIG. 6a contains, on the left hand side, a diagram with points showing the compositions of various thin films according to the invention containing Ir, Rh and Ru. The right hand diagram is a heat map showing the correlation between CSC and composition. The figure also contains an indication of what the surface structure is in the areas of the heat map with highest CSC.
Figure 6B:
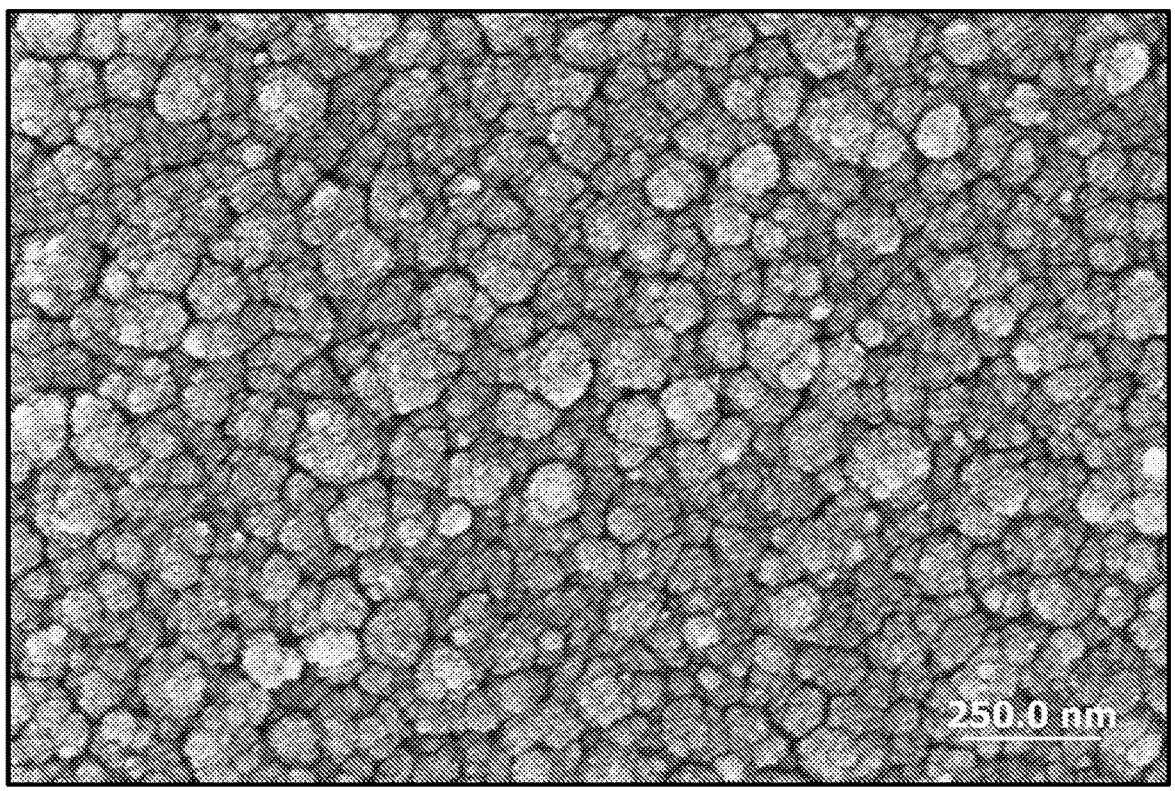
FIG. 6b is a 250 k× SEM micrograph of the surface of a $(Ir_{1-x}[RhRu]_x)_nO_{n+y}$ thin film according to the invention wherein x is 0.39, n is 1 and y is 1 prepared by reactive sputtering at 20% oxygen partial pressure.
Figure 6C:
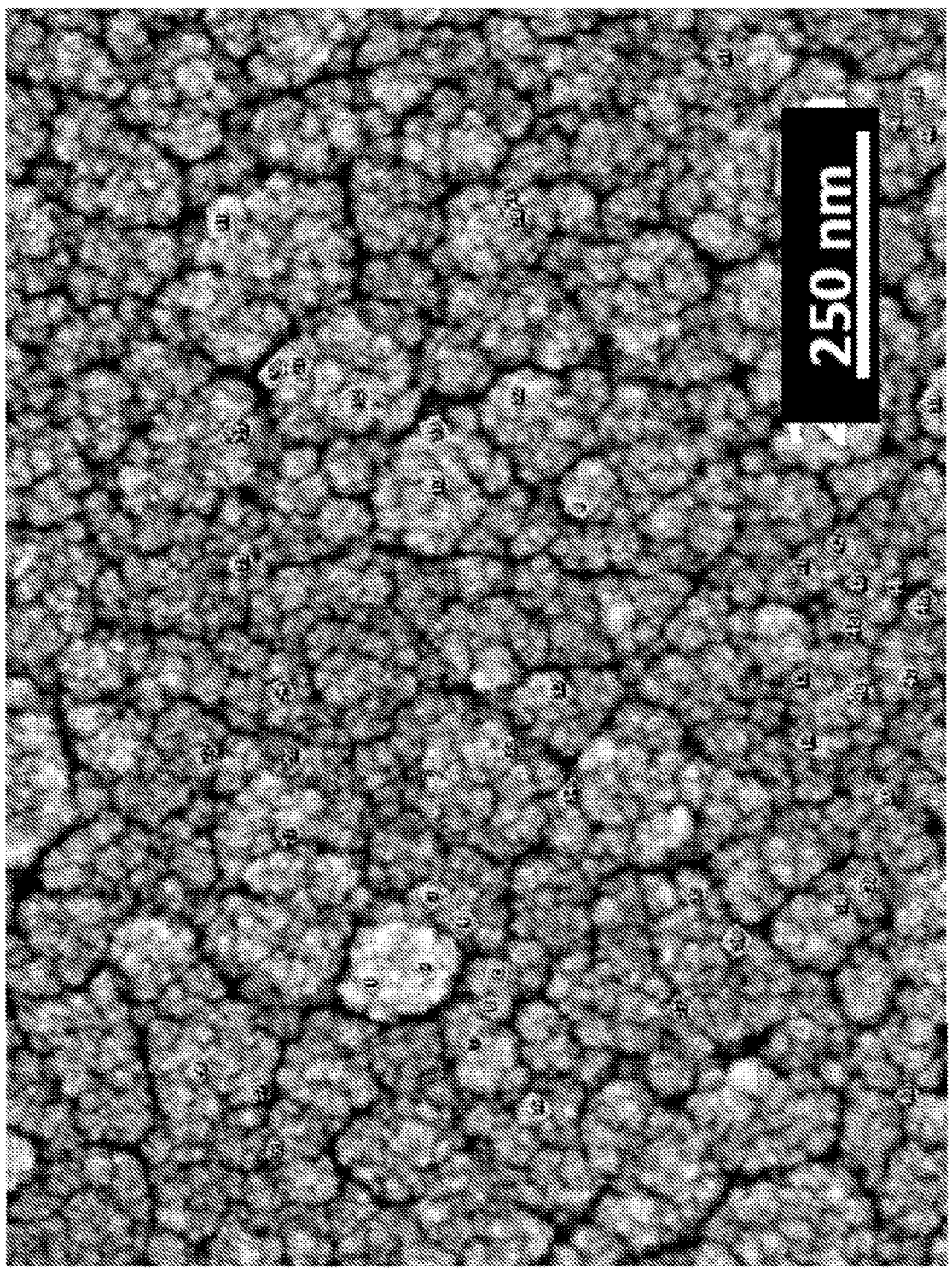
FIG. 6c is a 250 k× SEM micrograph of the surface of a $(Ir_{1-x}[RhRu]_x)_nO_{n+y}$ thin film according to the invention wherein x is 0.29, n is 1 and y is 1. prepared by reactive sputtering at 20% oxygen partial pressure. The grains used to measure average aspect ratio and average circularity are identified in the figure.
Figure 8:
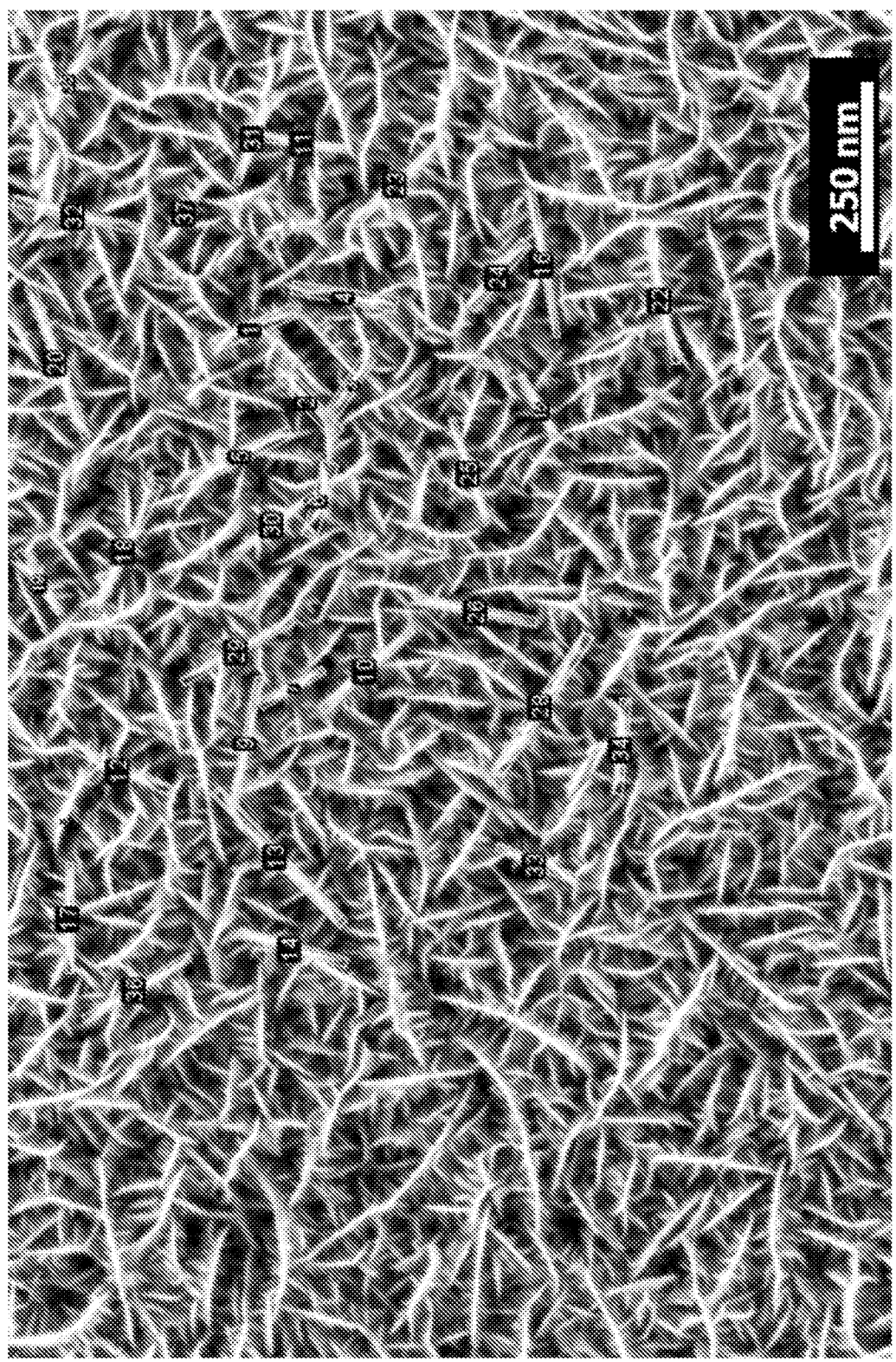
FIG. 8 is a SEM micrograph of the surface of an $IrO_2$ thin film sputtered at 80% oxygen partial pressure. The grains used to measure average aspect ratio and average circularity are identified in the figure.

Also, the grains preferably have a nanocrystalline grain size, i.e. the grains are less than 100 nm in any axis length, preferably less than 50 nm in any axis length. The dimensions required for determining aspect ratio, circularity and nanocrystalline size of the grain can be obtained by analyzing SEM images obtained, for example, using a JEOL-7500 scanning electron microscope (SEM), a LEO 1530 VP SEM, or other SEM with comparable imaging capabilities. The values provided are an average of at least 30 grains. The SEM micrographs may be analyzed using any conventional SEM image analysis software, such as ImageJ image analysis software, to determine that major and minor axes of grains and perimeter. Grains are distinguishable in a micrograph by the contrast that is present at grain boundaries, as shown in FIGS. 6c and 8.

The metal oxide materials of the first, third and fifth aspects of the invention which comprise Ir, M and/or M' can suitably be classified as solid solutions. In this context the term solid solution means that the metal oxide material has the crystal structure of a parent metal oxide containing a single metal species, in which a fraction of the known metal sites in that crystal structure contain other metals. Put another way, the material may be a solid solution based on the Hume-Rothery Rules. For example, the metal oxide materials may suitably adopt the tetragonal structure of IrO$_2$, the rutile structure, in which a fraction of the known Ir sites contain metals M and M' rather than Ir. The extent of the substitution of Ir with M and M' will depend on the amount of M and M' in the metal oxide material relative to Ir. Put another way, the solid solvent is IrO$_2$ and the solute is M and M'. Accordingly, the crystal structure of the metal oxide material remains the same as IrO$_2$, including any lattice distortion resulting from the different size of the metals M and M'. In the case of metal oxide materials which comprise Ir, M and M' in which M and M' are Rh, the metal oxide materials may also take the orthorhombic structure of Rh$_2$O$_3$, in which a fraction of the known Rh sites contain Ir. In the case of metal oxide materials which comprise Ir, M and M' in which M is Rh and M' is Ru, the system will be a substitutional solid solution based on the Hume-Rothery Rules which will take on the oxide structure of the stoichiometrically dominant metal in the ternary oxide. In the case of metal oxide materials which comprise Ir, M and M' in which M and M' are Pd, the metal oxide materials may also take cubic or tetragonal structure, depending on the ratio of Ir to Pd, in which a fraction of the known Pd sites contain Ir. When the stoichiometry of the metal oxide material is different from the stoichiometry required by the parent crystal structure, this can be rationalised by the presence of, for example, additional interstitial oxygen species in the lattice. Alternatively, there may be Ir, M or M' or oxygen vacancies in the lattice, preferably oxygen vacancies. Such vacancies or additional species can be detected using the conventional analytical techniques mentioned below. In the first, third and fifth aspects of the invention which comprise Ir, M and M', the Ir, M and M' in the metal oxide material generally have an oxidation state of 2$^+$, 3$^+$ or 4$^+$, including intermediate and partial oxidation states. The oxygen generally has an oxidation state of 2$^-$.

The thin film coatings of the first, second, third and fifth aspects of the invention may comprise more than one metal oxide material. Preferably, the thin film coatings comprise a single metal oxide material. It is within the capability of a skilled person to determine whether one or more metal oxide materials is/are present, and also the identity of the metal oxide material(s), using conventional analytical techniques. For example, a skilled person can use energy dispersive x-ray spectroscopy and/or x-ray diffraction spectroscopy. For example, correlation of composition measured by energy dispersive spectroscopy and crystal structure determined by locations of diffraction peaks are used to determine the presence of a metal oxide material. Generally, x-ray diffraction spectroscopy provides information about crystal structure, and energy dispersive x-ray spectroscopy provides information about the composition (e.g. ratio of I to M, M' and O). Mixtures of metal oxide materials are determined by indexing all diffraction peaks observed in x-ray diffraction spectra. The thin film coatings of the first, second, third and fifth aspects of the invention may also comprise small amounts (for example no more than 10%, preferably no more than 5%, more preferably no more than 1%) of other materials which contain metals Ir, M and M'. For example, metal oxides, hydroxides and species containing metal ions in different oxidation states, for example higher, as compared to those present in the metal oxide material. However, the thin film coatings predominantly contain more than one, preferably one, metal oxide material as defined in the first, second, third and fifth aspects of the invention. Put another way, the thin film coatings of the first, second, third and fifth aspects of the invention consist essentially of, preferably consist of, one or more, preferably one, of the metal oxide materials defined in the first, second, third and fifth aspects of the invention. The term "consists essentially of" takes its conventional meaning that the materials present other than the metal oxide material do not materially affect the essential characteristics of the thin film coating. For example, the thin film coating may comprise at least 90% metal oxide material (s), preferably at least 95%, more preferably at least 99% by weight of the thin film coating.

In a fourth aspect, the present invention provides a method for preparing the thin film coatings of the first, second and third aspects of the invention by reactive sputtering onto a substrate, wherein the oxygen partial pressure during reactive sputtering is at least 20%. The oxygen partial pressure during reactive sputtering is typically no more than 95%, preferably no more than 90%. As is conventional in the art, the substrate is the anode and the cathode(s) comprise(s) metal(s) M, M' and (if required) Ir. The gas used for sputtering comprises, preferably consists of, a mixture of oxygen and an inert gas, preferably nitrogen or argon or a mixture thereof. The inventors have surprisingly found that the inclusion of nitrogen in the sputtering gas can improve the microstructure of the surface of the thin film coatings accordingly further improving the suitability of the thin film coatings for use in implantable medical devices. This effect is especially realised in the case of thin film coatings comprising metal oxide materials of the invention in which M and M' are Rh. A suitable partial pressure of nitrogen is in the range of and including 5 to 30%, preferably 10 to 20%, and in this aspect nitrogen and oxygen are preferably the only sputtering gases.

The deposition pressure during sputtering is typically at least 1 mT, suitably at least 5 mT, preferably greater than 5 mT, for example at least 10 mT. The deposition pressure during sputtering is suitably no more than 100 mT, for example no more than 50 mT, preferably no more than 35 mT. Accordingly, the pressure may be, for example greater than 5 mT, for example at least 10 mT, but no more than 100 mT, suitably no more than 50 mT, preferably no more than 35 mT. The deposition temperature during sputtering is suitably at least 10° C., typically at least 15° C., preferably at least 20° C. Suitably, the deposition temperature is no more than 750° C., typically no more than 550° C., preferably no more than 450° C. The flow rate of the gas mixture during sputtering may be at least 10 sccm (standard cubic centimetres per minute), suitably at least 20 sccm, typically at least 40 sccm. The upper limit of flow rate is not particularly limited and depends on the equipment used. In some cases, the flow rate is suitably no more than 120 sccm, typically no more than 100 sccm. For example, the flow rate may be about 50 sccm but this is not limiting. Standard cubic centimetres per minute is a standard unit in the art of reactive sputtering, known to a skilled person. The flow is based on mass of the atom/molecule that goes through the mass flow controller. When a flow rate is defined as, for example, 20 sccm, the mass flow controller allows the flow of a mass equivalent to the mass of 20 cubic centimetres of the gas at 0° C. and 760 Torr (1 atm). Accordingly, when the mass flow controller is sitting at room temperature it is calibrated to allow for the flow of a mass equivalent to the mass of 20 cubic centimetres of the gas at 0° C. and 760 Torr (1 atm).

It is within the capabilities of a skilled person to select and set up apparatus for preparing a thin film coating according to the invention. Put another way, a skilled person is capable of configuring a sputtering chamber to deposit Ir, M and M' in an oxygen containing atmosphere to produce the thin film coatings of the invention. Moreover, a skilled person is capable of varying the oxygen partial pressure in the sputtering chamber as required by, for example, adjusting the individual argon and oxygen flow rates whilst maintaining the sum of the flow rates in the required ranges. This can be achieved by adjusting individual mass-flow controllers in the apparatus. The flow rate can be controlled, for example, by altering the pumping in the chamber or the power to the cathode and such control is within the capability of a skilled person. For example, the flow rate can be controlled by adjustment of a pressure controlling baffle valve which throttles the pumping effectiveness.

As is conventional in the art, prior to sputtering the chamber is evacuated. Suitably, the chamber is evacuated to a base pressure of less than $2\times10^{-7}$ Torr using a pump which may comprise, for example, a Leybold® 1000C turbo pump backed by an Alcatel Drytel® 34 dry pump.

The size and shape of the elemental targets Ir, M and M', Ru and Rh is not particularly limited. Suitable elemental targets may have a diameter in the range of and including 40 to 60 mm, for example about 50 mm and a thickness in the range of and including 2 to 4 mm, for example about 3 mm. The working distance between the cathode and the anode is also not particularly limited, with a suitable working distance being in the range of and including 50 to 100 mm, for example about 75 mm.

The sputtering source is typically a pulsed-DC power supply, for example Advanced Energy Pinnacle Plus® operated. The power, frequency, voltage and current used are not particularly limited. A suitable power is in the range of and including 50 to 150 W, for example about 100 W, a suitable frequency is in the range of and including 50 to 250 kHz, typically 100 to 180 kHz, for example about 140 kHz, and a reverse period of about 1 µs. The voltage may be on average 200 to 1000 V, typically 400 to 800 V, for example about 600 V, and the current may be 0.1 to 1.0 A, typically 0.1 to 0.3 A, for example about 0.2 A on the targets.

The atomic ratio of Ir to total metal M and M', and the atomic ratio of M to M' (when M and M' are different) can be controlled by adjusting the power supplied to each cathode. The sum of the power supplies is held constant and a suitable sum is in the range of and including 100 to 150 W, for example about 100 W.

A skilled person is aware of ways in which the temperature can be controlled during deposition. For example, the deposition temperature can be controlled using a resistive heater machined from a thin molybdenum sheet. A K-type thermocouple can be used as the temperature sensor. It is advantageous to position the sensor below the heater in a ceramic block. For example, the sensor can be placed so that the measured temperature matches the temperature measured on the surface of the substrate tray (above the heater)

using a pyrometer for example a LAND CYCLOPS® 153A. The positioning is typically performed at the minimum temperature for which the pyrometer is effective, for example a temperature of about 500° C. The temperature may be controlled using a thermocouple connected to a Honeywell® temperature controller.

The substrate onto which the thin film is coated, the anode in the sputtering chamber, will depend on what the intended application of the thin film is. The identity of the substrate is not particularly limited, provided it can receive a thin film coating according to the invention. Suitable materials when the thin film coating is an electrode (i.e. suitable materials in the electrode of the invention) include NiTi, W, Ta, MP35N nickel alloy, Ti-6Al-4V, Stainless Steel, Pt-10Ir, Pt and Au. A skilled person will be aware of suitable substrates for an electrode. In the case of a medical device comprising the electrode (i.e. suitable materials in the medical device of the invention) suitable materials include any material which is suitable for use in a medical device, preferably a biologically (i.e. in a human) implantable medical device. A skilled person will be aware of suitable substrates for a medical device. For example, the substrate for a medical device, preferably an implantable medical device, may also be NiTi, W, Ta, MP35N nickel alloy, Ti-6Al-4V, Stainless Steel, Pt-10Ir, Pt and Au.

The cathode may be pre-sputtered with the inert gas, preferably argon, to remove any layers of oxidation that may have formed on the surface of the target to better control deposition rates and coating composition. The conditions for pre-sputtering are not particularly limited. Suitably, the cathode may be pre-sputtered for a time in the range of and including 2 to 20 minutes at a power in the range of and including 25 to 75 W with an inert gas, preferably Ar, flow rate in the range of and including 25 to 75 sccm.

In a fifth aspect, the invention provides thin film coatings obtainable by the method of the fourth aspect of the invention. Put another way, the fifth aspect of the invention provides thin film coatings of the first, second or third aspects of the invention obtainable by the method of the fourth aspect of the invention.

In the fifth aspect of the invention, when the obtainable thin film is a thin film according to the first aspect of the invention, M and M' are Rh, and the oxygen partial pressure during reactive sputtering is greater than 60%, preferably at least 70%, for example about 80%, the atomic ratio of Ir to total metal M and M' is in the range of and including 20:1 to 1:20, preferably 3:2 to 1:3, for example 1:1. Also, the atomic ratio of oxygen to total metal species (Ir, M and M') is preferably in the range of and including 3:2 to 2:1, more preferably the atomic ratio of oxygen to total metal species (Ir, M and M') is 2:1. When the oxygen partial pressure during reactive sputtering is greater than 30% and no more than 60%, for example about 50%, the atomic ratio of Ir to total metal M and M' is suitably in the range of and including 4:1 to 1:20, typically 1:1 to 1:20, for example 1:4 to 1:20. Also, the atomic ratio of oxygen to total metal species (Ir, M and M') is preferably in the range of and including 3:2 to 2:1, more preferably the atomic ratio of oxygen to total metal species (Ir, M and M') is 2:1. When the oxygen partial pressure during reactive sputtering is in the range of and including 20 to 30%, for example about 20%, the atomic ratio of Ir to total metal M and M' is suitably in the range of and including 1:4 to 1:20. Also, the atomic ratio of oxygen to total metal species (Ir, M and M') is preferably in the range of and including 3:2 to 2:1, more preferably the atomic ratio of oxygen to total metal species (Ir, M and M') is 2:1. The inventors have surprisingly found that the inclusion of nitrogen in the sputtering gas can especially improve the microstructure of the surface of these thin film coatings accordingly further improving the suitability of the thin film coatings for use in implantable medical devices. A suitable partial pressure of nitrogen is in the range of and including 5 to 30%, preferably 10 to 20%, and in this aspect nitrogen and oxygen are preferably the only sputtering gases.

In the fifth aspect of the invention, when the obtainable thin film is a thin film according to the first aspect of the invention and M and M' are Rh, a preferred thickness is in the range of and including 100 to 500 nm, suitably 200 to 400 nm, for example about 250 nm. Accordingly, in an example of a preferred thin film coating, the oxygen partial pressure during reactive sputtering is at least 70%, the atomic ratio of Ir to total metal M and M' is in the range of and including 3:2 to 1:3, preferably 1:1, the atomic ratio of oxygen to total metal species (Ir, M and M') is 2:1, and the thickness is in the range of and including 200 to 400 nm, preferably about 250 nm.

In the fifth aspect of the invention, when the obtainable thin film is a thin film according to the first aspect of the invention, M and M' are Ru and the oxygen partial pressure during reactive sputtering is greater than 60%, preferably at least 70%, for example about 80%, the atomic ratio of Ir to total metal M and M' is in the range of and including 20:1 to 1:20, suitably 3:1 to 1:2. Also, the atomic ratio of oxygen to total metal species (Ir, M and M') is preferably in the range of and including 2:1 to 4:1, more preferably the atomic ratio of oxygen to total metal species (Ir, M and M') is 2:1. When the oxygen partial pressure during reactive sputtering is greater than 30% and no more than 60% for example about 50%, the atomic ratio of Ir to total metal M and M' is suitably the range of and including 3:1 to 1:20, typically 1:1 to 1:20, for example 1:2 to 1:20. Also, the atomic ratio of oxygen to total metal species (Ir, M and M') may be in the range of and including 2:1 to 4:1, preferably 2:1 to 3:1, more preferably the atomic ratio of oxygen to total metal species (Ir, M and M') is 2:1. When the oxygen partial pressure during reactive sputtering is in the range of and including 20% to 30%, for example about 20%, the atomic ratio of Ir to total metal M and M' is suitably in the range of and including 1:1 to 1:20, for example 1:4 to 1:20. Also, the atomic ratio of oxygen to total metal species (Ir, M and M') may be in the range of and including 2:1 to 4:1, preferably 2:1 to 3:1, more preferably the atomic ratio of oxygen to total metal species (Ir, M and M') is 2:1.

In the fifth aspect of the invention, when the obtainable thin film is a thin film according to the first aspect of the invention and M and M' are Ru, a preferred thickness is in the range of and including 100 to 500 nm, suitably 100 to 200 nm, for example about 100 nm or about 200 nm. Accordingly, in an example of a preferred thin film coating, the oxygen partial pressure during reactive sputtering is at least 70%, the atomic ratio of Ir to total metal M and M' is in the range of and including 3:1 to 1:2 to 3:1, 3:1 or 1:2, the atomic ratio of oxygen to total metal species (Ir, M and M') is 2:1, and the thickness is in the range of and including 100 to 200 nm, for example 100 nm or 200 nm.

In the fifth aspect of the invention, when the obtainable thin film is a thin film according to the first aspect of the invention, M and M' are Pd and the oxygen partial pressure during reactive sputtering is greater than 60%, preferably at least 70%, for example about 80%, the atomic ratio of Ir to total metal M and M' is preferably in the range of and including 1:2 to 1:9. Also, the atomic ratio of oxygen to total metal species (Ir, M and M') is preferably in the range of and including 2:1 to 4:1, more preferably the atomic ratio of oxygen to total metal species (Ir, M and M') is 2:1. When the oxygen partial pressure during reactive sputtering is greater than 30% and no more than 60% for example about 50%, the atomic ratio of Ir to total metal M and M' is preferably in the range of and including 1:2 to 1:9. Also, the atomic ratio of oxygen to total metal species (Ir, M and M') may be in the range of and including 2:1 to 4:1, preferably 2:1 to 3:1, more preferably the atomic ratio of oxygen to total metal species (Ir, M and M') is 2:1. When the oxygen partial pressure during reactive sputtering is in the range of and including 20% to 30%, for example about 20%, the atomic ratio of Ir to total metal M and M' is preferably in the range of and including 1:2 to 1:9. Also, the atomic ratio of oxygen to total metal species (Ir, M and M') may be in the range of and including 2:1 to 4:1, preferably 2:1 to 3:1, more preferably the atomic ratio of oxygen to total metal species (Ir, M and M') is 2:1.

In the fifth aspect of the invention, when the obtainable thin film is a thin film according to the first aspect of the invention and M and M' are Pd, a preferred thickness is in the range of and including 100 to 500 nm, suitably 100 to 200 nm, for example about 100 nm or about 200 nm. Accordingly, in an example of a preferred thin film coating, the oxygen partial pressure during reactive sputtering is at least 70%, the atomic ratio of Ir to total metal M and M' is in the range of and including 1:2 to 1:9, the atomic ratio of oxygen to total metal species (Ir, M and M') is 2:1, and the thickness is in the range of and including 100 to 200 nm, for example 100 nm or 200 nm. In another example of a preferred thin film coating, the oxygen partial pressure during reactive sputtering is greater than 30% and no more than 60%, the atomic ratio of Ir to total metal M and M' is in the range of and including 1:2 to 1:9, the atomic ratio of oxygen to total metal species (Ir, M and M') is 2:1, and the thickness is in the range of and including 100 to 200 nm. In another example of a preferred thin film coating, the oxygen partial pressure during reactive sputtering is in the range of and including 20% to 30%, the atomic ratio of Ir to total metal M and M' is in the range of and including 1:2 to 1:9, the atomic ratio of oxygen to total metal species (Ir, M and M') is 2:1, and the thickness is in the range of and including 100 to 200 nm, for example 100 nm or 200 nm.

In the fifth aspect of the invention, when the obtainable film is a thin film according to the second aspect of the invention and the metal oxide material is $Rh_{a-1}O_a$, the oxygen partial pressure during sputtering is at least 20%, suitably no more than 90%. When the oxygen partial pressure during reactive sputtering is greater than 60% a is preferably 2. When the oxygen partial pressure during reactive sputtering is no more than 60%, a is preferably 3. When the metal oxide material is $RuO_b$, the oxygen partial pressure during sputtering is at least 20%, suitably no more than 90%, preferably no more than 50%. When the oxygen partial pressure during reactive sputtering is greater than 60%, b is preferably 4. When the oxygen partial pressure during reactive sputtering is no more than 60%, b is preferably 2.

In the fifth aspect of the invention, when the obtainable film is a thin film according to the third aspect of the invention M and M' are Rh and the oxygen partial pressure during reactive sputtering is at least at least 60%, preferably at least 70%, for example about 80%, x is in the range of and including 0.05 to 0.95, preferably 0.4 to 0.75. Also, n is in the range of and including 1 to 2, for example 1 or 2, preferably 1, and y is preferably 1. When the oxygen partial pressure during reactive sputtering is greater than 30% and no more than 60%, for example about 50%, x is suitably in the range of and including 0.2 to 0.95, typically 0.5 to 0.95, for example 0.8 to 0.95. Also, n is in the range of and including 1 to 2, for example 1 or 2, preferably 1, and y is preferably 1. When the oxygen partial pressure during reactive sputtering is in the range of and including 20% to 30%, for example about 20%, x is preferably in the range of and including 0.8 to 0.95. Also, n is in the range of and including 1 to 2, for example 1 or 2, preferably 1, and y is preferably 1. The inventors have surprisingly found that the inclusion of nitrogen in the sputtering gas can especially improve the microstructure of the surface of these thin film coatings accordingly further improving the suitability of the thin film coatings for use in implantable medical devices. A suitable partial pressure of nitrogen is in the range of and including 5 to 30%, preferably 10 to 20%, and in this aspect nitrogen and oxygen are preferably the only sputtering gases.

In the fifth aspect of the invention, when the obtainable thin film is a thin film according to the third aspect of the invention and M and M' are Rh, a preferred thickness is in the range of and including 100 to 500 nm, suitably 200 to 400 nm, for example about 250 nm. Accordingly, in an example of a preferred thin film coating, the oxygen partial pressure during reactive sputtering is at least 70%, x is in the range of and including 0.4 to 0.75, for example 0.5, n is 1 and y is 1, and the thickness is in the range of and including 200 to 400 nm, preferably about 250 nm.

In the fifth aspect of the invention, when the obtainable film is a thin film according to the third aspect of the invention, M and M' are Ru and the oxygen partial pressure during reactive sputtering is at least 60%, preferably at least 70%, for example about 80%, x is in the range of and including 0.05 to 0.95, typically 0.25 to 0.65. Also, n is preferably 1 and y is in the range of and including 1 to 3, for example 1, 2 or 3, preferably 1. When the oxygen partial pressure during reactive sputtering is greater than 30% and no more than 60%, x is preferably in the range of and including 0.25 to 0.95, typically 0.50 to 0.95, for example 0.8 to 0.95. Also, n is preferably 1 and y is in the range of and including 1 to 3, for example 1, 2 or 3, preferably 1 or 2, more preferably 1. When the oxygen partial pressure during reactive sputtering is in the range of and including 20% to 30%, for example 20% x is preferably in the range of and including 0.5 to 0.95, for example 0.8 to 0.95. Also, n is preferably 1 and y is in the range of and including 1 to 3, for example 1, 2 or 3, preferably 1 or 2, more preferably 1.

In the fifth aspect of the invention, when the obtainable thin film is a thin film according to the third aspect of the invention and M and M' are Ru, a preferred thickness is in the range of and including 100 to 500 nm, suitably 100 to 200 nm, for example about 100 nm or about 200 nm. Accordingly, in an example of a preferred thin film coating, the oxygen partial pressure during reactive sputtering is at least 70%, x is in the range of and including 0.25 to 0.65, for example 0.25 or 0.65, n is 1 and y is 1, and the thickness is in the range of and including 100 to 200 nm, for example about 100 nm or about 200 nm.

In the fifth aspect of the invention, when the obtainable thin film is a thin film according to the third aspect of the invention, M is Rh and M' is Ru (or M is Ru and M' is Rh), the thickness may be in the range of and including 100 to 2000 nm. In an example of a preferred thin film coating, the oxygen partial pressure during reactive sputtering is at least 70%, x is in the range of and including 0.45 to 0.75, for example 0.65, n is 1 and y is 1, and the thickness is in the range of and including 100 to 2000 nm, for example about 1000 nm.

In the fifth aspect of the invention, when the obtainable film is a thin film according to the third aspect of the invention when x is 1, M and M' are Rh and the oxygen partial pressure during reactive sputtering is at least, preferably greater than, 60%, n is preferably 1 and y is preferably 1. When the oxygen partial pressure during reactive sputtering is no more than 60%, n is preferably 2 and y is preferably 1. In the fifth aspect of the invention, when the obtainable film is a thin film according to the third aspect of the invention when x is 1, M and M' are Ru and the oxygen partial pressure during reactive sputtering is at least 60%, n is preferably 1 and y is preferably 3. In the fifth aspect of the invention, when the obtainable film is a thin film according to the third aspect of the invention when x is 1, M and M' are Ru and the oxygen partial pressure during reactive sputtering is no more than 60%, n is preferably 1 and y is preferably 1.

In the fifth aspect of the invention, when the obtainable film is a thin film according to the third aspect of the invention, M and M' are Pd and the oxygen partial pressure during reactive sputtering is at least 60%, preferably at least 70%, for example about 80%, x is preferably in the range of and including 0.65 to 0.90. Also, n is preferably 1 and y is in the range of and including 1 to 3, for example 1, 2 or 3, preferably 1. When the oxygen partial pressure during reactive sputtering is greater than 30% and no more than 60%, x is preferably in the range of and including 0.65 to 0.90. Also, n is preferably 1 and y is in the range of and including 1 to 3, for example 1, 2 or 3, preferably 1 or 2, more preferably 1. When the oxygen partial pressure during reactive sputtering is in the range of and including 20% to 30%, for example 20% x is preferably in the range of and including 0.65 to 0.90. Also, n is preferably 1 and y is in the range of and including 1 to 3, for example 1, 2 or 3, preferably 1 or 2, more preferably 1.

In the fifth aspect of the invention, when the obtainable thin film is a thin film according to the third aspect of the invention and M and M' are Pd, a preferred thickness is in the range of and including 100 to 1000 nm, suitably 100 to 200 nm, for example about 100 nm or about 200 nm. Accordingly, in an example of a preferred thin film coating, the oxygen partial pressure during reactive sputtering is at least 70%, x is in the range of and including 0.65 to 0.90, n is 1 and y is 1, and the thickness is in the range of and including 100 to 200 nm, for example about 100 nm or about 200 nm. In another example of a preferred thin film coating, the oxygen partial pressure during reactive sputtering is greater than 30% and no more than 60%, x is in the range of and including 0.65 to 0.90, n is 1 and y is 1, and the thickness is in the range of and including 100 to 200 nm, for example about 100 nm or about 200 nm. In another example of a preferred thin film coating, the oxygen partial pressure during reactive sputtering is in the range of and including 20% to 30%, x is in the range of and including 0.65 to 0.90, n is 1 and y is 1, and the thickness is in the range of and including 100 to 200 nm, for example about 100 nm or about 200 nm.

The thin film coatings of the first, second, third or fifth aspects of the invention are preferably electrodes. Accordingly, the present invention provides an electrode comprising a thin film coating of the first, second, third and fifth aspects of the of the invention. The electrode may also be called an electrode track. The type, size and geometry of the electrode is not particularly limited and will depend on the intended application. A skilled person is capable of preparing an electrode according to the invention having the desired type, size and geometry. As discussed previously, a benefit of the invention is that the electrode can be miniaturised with respect to the same electrodes prepared by other materials. The electrode is preferably in a medical device and so the present invention also provides a medical device comprising the electrode of the invention. In particular, the medical device is implantable, for example biologically implantable. An implantable medical device is a device which can be placed on the surface of, or preferably inside, the body, preferably the human body. Also, the invention provides the use of a thin film according to the first, second, third or fifth aspects of the invention in a medical device. Also, the present invention provides the use of an electrode of the invention in a medical device. In particular, the medical device in both of these uses is implantable, for example biologically implantable.

The medical device of the invention, and in the uses of the invention, may be a diagnostic device. Also, for example, the medical device may be a cortical visual prosthesis, prosthetic limb, sacral nerve stimulator, spinal cord stimulator, gastric electric stimulator, deep brain stimulator, valgus nerve stimulator, electrophysiology catheter, cochlear implant, neurostimulator or a cardiac rhythm management device. Preferably, the medical device is a neurostimulator or a cardiac rhythm management device.

EXAMPLES

General Experimental Procedure (GEP)
1—Coatings Containing a Single Metal

Thin films were deposited on 316 stainless steel at room temperature. The substrates were placed on a stainless steel sample holder machined with recessed positions for the substrates, so they would remain stationary when inserted through the load lock into the deposition chamber and upon rotation under the cathode, allowing them to be coated in a single deposition.

The sputtering chamber was evacuated to a base pressure of $<2\times10^{-7}$ Torr with a Leybold 1000C turbo-pump backed by an Alcatel Drytel 34 dry pump. A 50.8 mm diameter, 3.175 mm thick elemental metal target was used as the cathode with a working distance of approximately 75 mm. A pulsed-DC power supply (Advanced Energy Pinnacle Plus) at a power of 100 W, a frequency of 140 kHz, and a reverse period of 1 μs was used as the sputtering source (~42% duty cycle). This resulted in an average of 600 V (60 V reverse bias) and 0.22 A on the target at a deposition pressure of 10 mTorr.

With a total flow rate of Ar and $O_2$ at 50 sccm (standard cubic centimeters per minute), the "downstream" pressure-controlling baffle valve that throttled the pumping effectiveness was at a position of approximately 20% open. All substrates were etched using an RF-power supply (ENI ACG-6B) running at 100 W with an Ar flow rate of 50 sccm for 5 minutes prior to deposition to improve coating adhesion. The cathode was pre-sputtered for 5 minutes at 50 W with an Ar flow rate of 50 sccm to remove any layers of oxidation that may have formed on the surface of the target to better control deposition rates and coating composition.

The deposition temperature was controlled using a resistive heater machined from a thin molybdenum sheet. A K-type thermocouple was used as the temperature sensor. The sensor was positioned below the heater in a ceramic block. Its specific placement was determined so that its measured temperature matched the temperature measured on the surface of the stainless-steel substrate tray (above the heater) using a pyrometer (LAND CYCLOPS 153A). The positioning was performed at a temperature of 500° C.—the minimum temperature where the pyrometer was effective. The temperature was controlled by connecting the thermocouple to a Honeywell DCP 216 temperature controller.

General Experimental Procedure (GEP)
2—Coatings Containing More Than One Metal

Thin films were deposited on 316 stainless steel at room temperature. The substrates were placed on a stainless steel sample holder machined with recessed positions for the substrates, so they would remain stationary when inserted through the load lock into the deposition chamber and upon rotation under the cathode, allowing them to be coated in a single deposition.

The sputtering chamber was evacuated to a base pressure of $<2\times10^{-7}$ Torr with a Leybold 1000C turbo-pump backed by an Alcatel Drytel 34 dry pump. 50.8 mm diameter, 3.175 mm thick elemental metal targets were used as the cathode with a working distance of approximately 75 mm. A pulsed-DC power supply (Advanced Energy Pinnacle Plus) with a frequency of 140 kHz, and a reverse period of 1 μs was used as the sputtering source (~42% duty cycle) for the Ir target, while a DC power supply (MDX-1000) was used for the other metal(s) target. The sum of the powers between both power supplies was held constant at 100 W (Pulsed DC+DC=100 W) and the amount of power supplied to each cathode was varied between depositions to achieve various coating compositions. This resulted in an average of 600 V (60 V reverse bias) and 0.22 A on the target at a deposition pressure of 10 mTorr. With a total flow rate of Ar and $O_2$ at 50 sccm, the "downstream" pressure-controlling baffle valve that throttled the pumping effectiveness was at a position of approximately 20% open.

The coatings were synthesized by co-sputtering from elemental metal targets in an $O_2$/Ar gas mixture (or as otherwise specified). The atomic ratio of metals was controlled by adjusting the power supplied to each cathode. With a total flow rate of Ar and $O_2$ at 50 sccm, the "downstream" pressure controlling baffle valve that throttled the pumping effectiveness was at a position of approximately 20% open. The substrates were etched using an RF-power supply running at 100 W for 5 minutes prior to deposition to improve adhesion. Each cathode was pre-sputtered for 5 minutes at 50 W with an Ar flowrate of 50 sccm to remove any layers of oxidation that may have formed on the surface of the target to better control deposition rates and coating composition.

The deposition temperature was controlled using a resistive heater machined from a thin molybdenum sheet. A K-type thermocouple was used as the temperature sensor. The sensor was positioned below the heater in a ceramic block. Its specific placement was determined so that its measured temperature matched the temperature measured on the surface of the stainless-steel substrate tray (above the heater) using a pyrometer (LAND CYCLOPS 153A). The positioning was performed at a temperature of 500° C.—the minimum temperature where the pyrometer was effective. The temperature was controlled by connecting the thermocouple to a Honeywell DCP 216 temperature controller.

Analysis Methods

The CSC of the films is a measure of the coating effectiveness for charge exchange between the ion-containing solution and the underlying electrode. The CSC was evaluated by cyclic voltammetry (CV) measurements in phosphate-buffered saline solution (PBS, pH=7.2, diluted from Amresco Pure PBS, 10×, USP Sterile) with a Metrohm Autolab PGSTAT204 potentiostat/galvanostat. In a three-electrode electrochemical system, the coating was the working electrode, while a Pt wire and a Ag/AgCl electrode were used as the counter and reference electrodes, respectively. The voltage was swept between the potentials of −0.6 to 0.8 V at a scan rate of 0.1 V/s.

The half-reaction of $IrO_2$ in PBS solution can be described by equation (1):

$$Ir(OH)_x(s) \Leftrightarrow IrO_x(s) + xH^+(aq) + xe^- \quad (1)$$

where the maximum value of x is 2.

The half-reaction for films containing Ir and Rh in PBS solution can be described by equations:

$$Ir(OH)_x(s) \Leftrightarrow IrO_x(s) + xH^+(aq) + xe^-$$
$$Rh(OH)_x(s) \Leftrightarrow RhO_x(s) + xH^+(aq) + xe^-$$

where the maximum value of x is 2.

The half-reaction for films containing Ir and Ru in PBS solution can be described by equations:

$$Ir(OH)_x(s) \Leftrightarrow IrO_x(s) + xH^+(aq) + xe^-$$
$$Ru(OH)_x(s) \Leftrightarrow RuO_x(s) + xH^+(aq) + xe^-$$

where the maximum value of x is 2.

The half-reactions for films containing Ir, Rh and Ru in PBS solution can be described by equations:

$$Ir(OH)_x(s) \Leftrightarrow IrO_x(s) + xH^+(aq) + xe^-$$
$$RhRu(OH)_x(s) \Leftrightarrow RhRuO_x(s) + xH^+(aq) + xe^-$$
$$(RhRu)_2(OH)_y(s) \Leftrightarrow (RhRu)_2O_y(s) + yH^+(aq) + ye^-$$

where the maximum value of x is 2 and y is 3.

The half-reaction for films containing Ir and Pd in PBS solution can be described by equations:

$$Ir(OH)_x(s) \Leftrightarrow IrO_x(s) + xH^+(aq) + xe^-$$
$$Pd(OH)_x(s) \Leftrightarrow PdO_x(s) + xH^+(aq) + xe^-$$

where the maximum value of x is 2.

The half-reaction for films containing Rh in PBS solution can be described by equations:

$$Rh(OH)_x(s) \Leftrightarrow RhO_x(s) + xH^+(aq) + xe^-$$
$$Rh_2(OH)_y(s) \Leftrightarrow Rh_2O_y(s) + xH^+(aq) + xe^-$$

where the maximum value of x is 2 and y is 3.

The half-reaction for films containing Ru in PBS solution can be described by equations:

$$Ru(OH)_x(s) \Leftrightarrow RuO_x(s) + xH^+(aq) + xe^-$$

where the maximum value of x is 2.

The exchanged charge is measured by cyclic voltammetry and is calculated from the area enclosed by the C-V curve between voltage sweep directions with known scan rates. This area can be calculated to yield the total CSC of the coating using the expression:

$$CSC\left(\frac{mC}{cm^2}\right) = \frac{1}{v_s}\int_{-0.6}^{0.8}|j|\,dV \quad (2)$$

where j is the current density measured in mA/cm², and $v_s$ is the voltage sweep rate. A numerical integration algorithm embedded in Kaleidagraph by Synergy Software was used to integrate the area enclosed by the C-V curve.

Microstructural studies were performed on a JEOL-7500 scanning electron microscope (SEM) or a LEO 1530 VP SEM.

For energy dispersive spectroscopy, coatings were deposited on stainless steel plates (6.35×6.35×2 mm) and placed in a Thermo Fisher Scientific Apreo SEM. Samples were subsequently analysed with an Oxford Instruments Energy Dispersive Spectrometer under vacuum with an acceleration voltage of 10 kV, beam current of 30 nA, and a working distance of approximately 10 mm. Atomic composition of coatings were measured using AZtec Oxford Instrument software.

For XRD analysis coatings were deposited on stainless steel plates (6.35×6.35×2 mm) and placed in a Malvern-Panalytical Empyrean XRD. The coatings were exposed to a parallel beam X-Ray source with power 45 kV and current 40 mA at a diffraction angle range of 20-80 degrees. Angle range and resultant diffraction data was determined and analysed using Malvern Panalytical X'Per HighScore Plus software.

The dimensions required for determining aspect ratio, circularity and nanocrystalline size of the grain can be obtained by analyzing SEM images obtained for example using a JEOL-7500 scanning electron microscope (SEM), a LEO 1530 VP SEM, or other SEM with comparable imaging capabilities. The values provided are an average of at least 30 grains. The SEM micrographs may be analyzed using any conventional SEM image analysis software, such as ImageJ image analysis software to determine that major and minor axes of grains and perimeter. Grains are distinguishable in a micrograph by the contrast that is present at grain boundaries, as shown in FIGS. 6c and 8.

Figure 10:
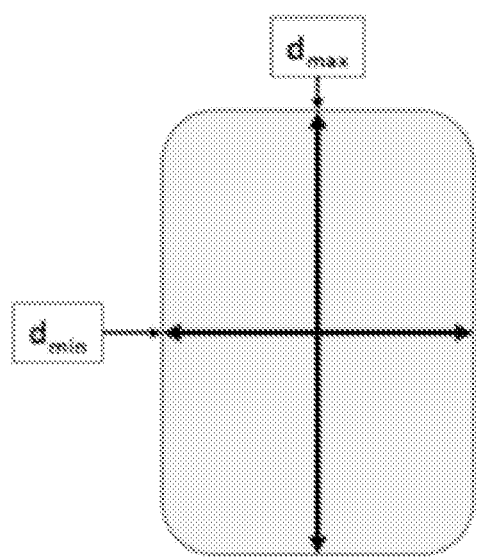
FIG. 10 shows how aspect ratio is the ratio of the length of the minor axis to the length of an orthogonal major axis, and equiaxed grains would approach an aspect ratio of 1.

As illustrated in FIG. 10, aspect ratio is the ratio of the length of the minor axis to the length of an orthogonal major axis, equiaxed grains would approach an aspect ratio of 1:

Circularity is a measure of how close an object is to being a true circle, which is a function of perimeter (P) and area (A). A spherical grain would have a circularity factor approaching 1 (P=2πr; A=πr²):

$$F_C = \frac{4\pi A}{P^2}$$

IrO₂ Films (Comparative)

Results

In reference [5], sputtered IrO₂ thin films are prepared having charge storage capacity (CSC) values which are better than industry standard films, [7] [8]. A low sputtering pressure of 5 mTorr led to films with an acceptable surface. Increasing the total pressure during sputtering resulted in the provision of surfaces consisting of unstable "platelet" formations. Such formations have conventionally been avoided in industry films by, for example, sputtering pure Ir and activating through voltage cycling or using very low (for example below 20%) oxygen partial pressures during reactive sputtering.

The present inventors investigated modifying the CSC properties and surface structure in IrO₂ films by varying oxygen partial pressure during sputtering. Accordingly, IrO₂ films were prepared by reactive sputtering using Ar and at various O₂ partial pressures and measured for CSC.

As shown in FIG. 1a, the CSC of IrO₂ increases to a value of between 30 mC/cm² and 35 mC/cm² when the film is sputtered at a high O₂ partial pressure (80%). However, when the films are prepared at an O₂ partial pressure of greater than about 30%, a "platelet" microstructure forms on the surface. This microstructure is shown in the SEM image in FIG. 1b. Films having this surface structure are less suitable for use in implantable medical components because the "platelets" easily break down and fall away from the film.

FIG. 8 is an SEM image of the surface of an IrO₂ film. The surface has an unsuitable "platelet" otherwise known as "nanoflake" microstructure. The figure illustrates grains used to identify average aspect ratio and average circularity. On this surface, average aspect ratio is 0.092±0.040 and average circularity is 0.185±0.064.

Experimental Procedure

Thin films were deposited in accordance with GEP 1 with an elemental Ir cathode target.

For investigation of the role of oxygen partial pressure, the relative Ar and O₂ flow rates were adjusted. The sum of the flow rates was held at a constant flow of 50 sccm, but the individual mass-flow controllers were varied to adjust the content of O₂ from 5%, 10%, 20%, 30%, 40%, 50%, 60%, 70%, 80% O₂ partial pressure (as shown in FIG. 1a). The thickness of the films in FIG. 1a was in the range of 170 to 450 nm, and the thickness of the film in FIG. 1b was 800 nm (sputtered at 35% oxygen partial pressure). The cathode power was again held constant at 100 W.

Oxide Films Containing Ir and Rh

Results

Oxide films containing Ir and Rh were prepared at various thicknesses, and with varying Ir and Rh content, by reactive sputtering using Ar, and at 20%, 50% and 80% O₂ partial pressures and measured for CSC. The results are shown in FIG. 2a.

Figure 2A:
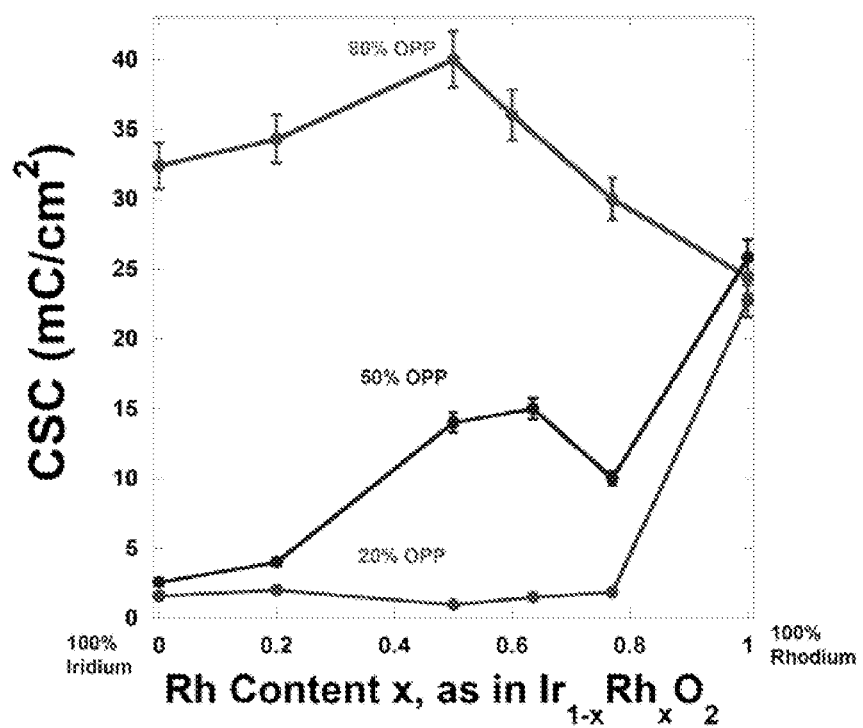
FIG. 2a is a chart showing charge storage capacities for thin film coatings $(Ir_{1-x}Rh_x)O_2$ according to the invention at various atomic percentages of Ir and Rh, prepared by reactive sputtering at 20, 50 and 80% oxygen partial pressure.

As shown in FIG. 2a, the CSC of oxide films containing Ir and Rh can be significantly increased by increasing the O₂ partial pressure used to synthesize the films, as well as controlling the atomic ratio of Ir to Rh in the material.

Figure 1B:
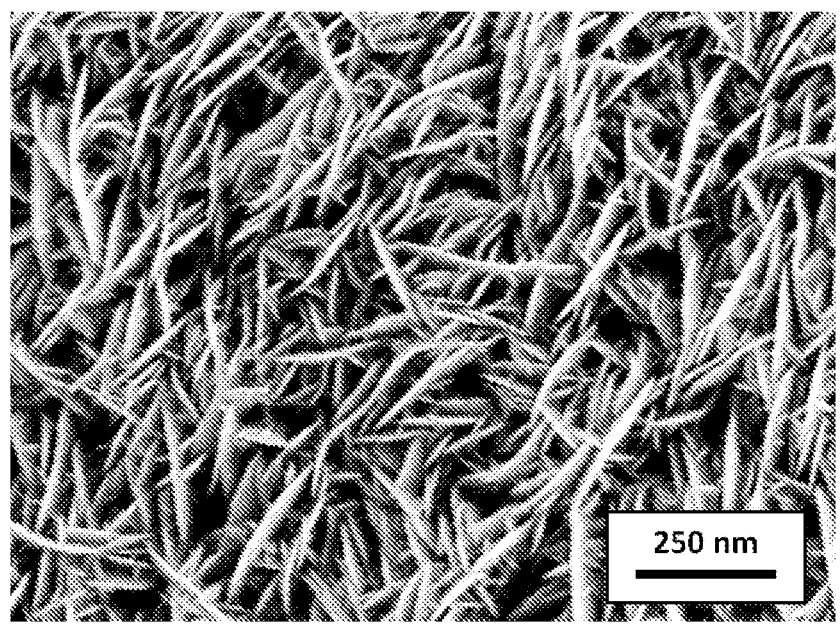
FIG. 1b is a 250 kx (i.e. 250,000 times magnification) SEM micrograph of the surface of an $IrO_2$ thin film sputtered at 35% oxygen partial pressure.
Figure 2B:
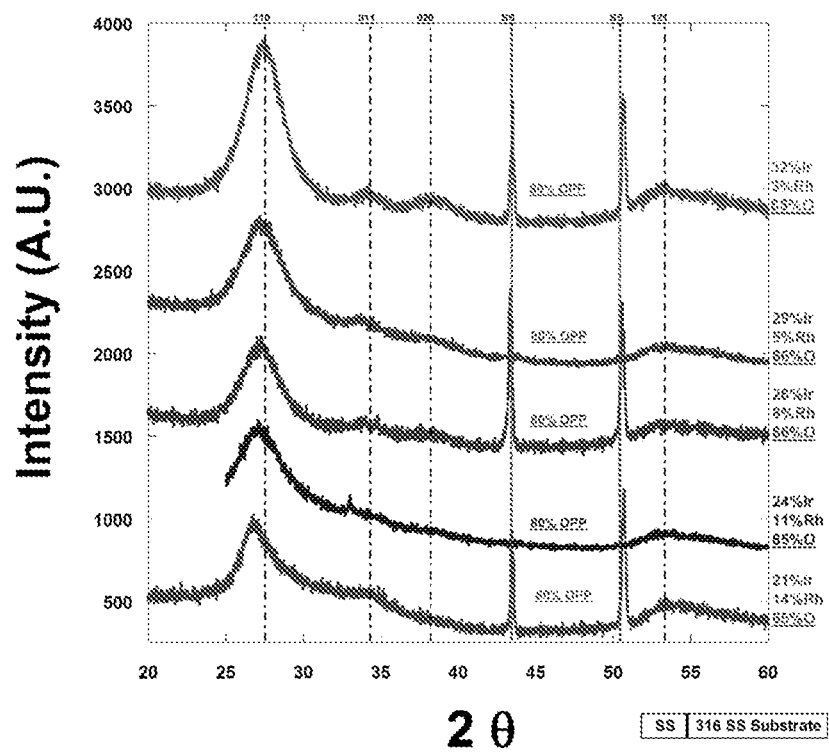
FIG. 2b shows a set of XRD spectra for five thin film coatings $(Ir_{1-x}Rh_x)_nO_{n+y}$ prepared by reactive sputtering at 80% oxygen partial pressure. The percentages of Ir, Rh and oxygen are provided by each spectra.
Figure 2C:
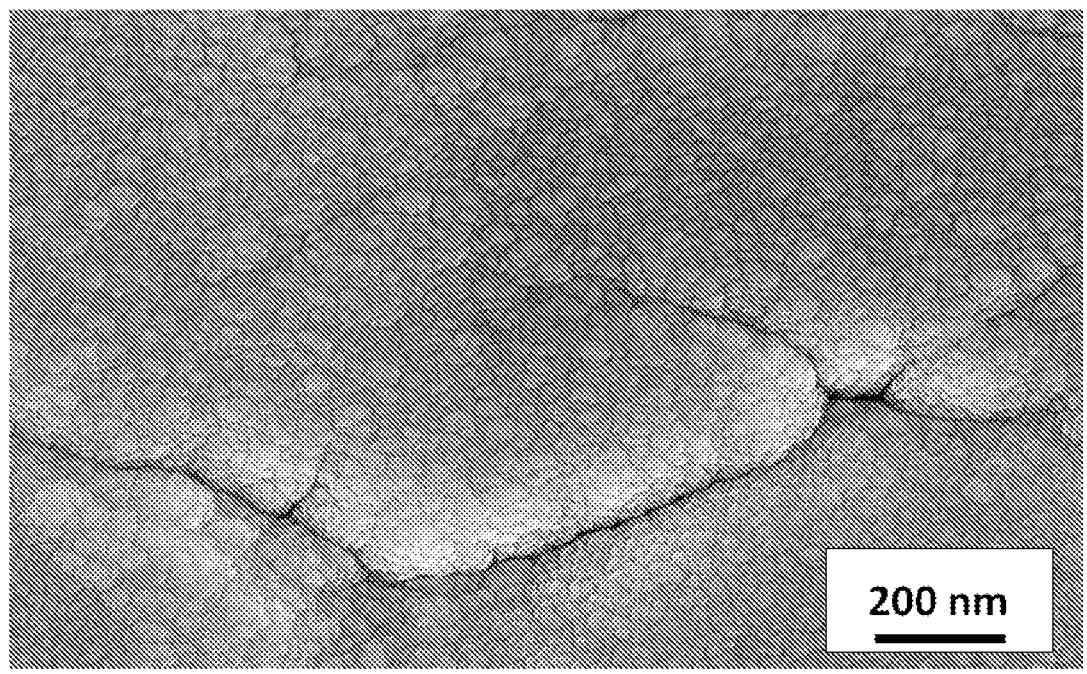
FIG. 2c is a 250 k× SEM micrograph of the surface of a $(Ir_{1-x}Rh_x)_nO_{n+y}$ thin film according to the invention wherein x is 0.75, n is 1.5 and y is 1 prepared by reactive sputtering at 20% oxygen partial pressure.
Figure 2D:
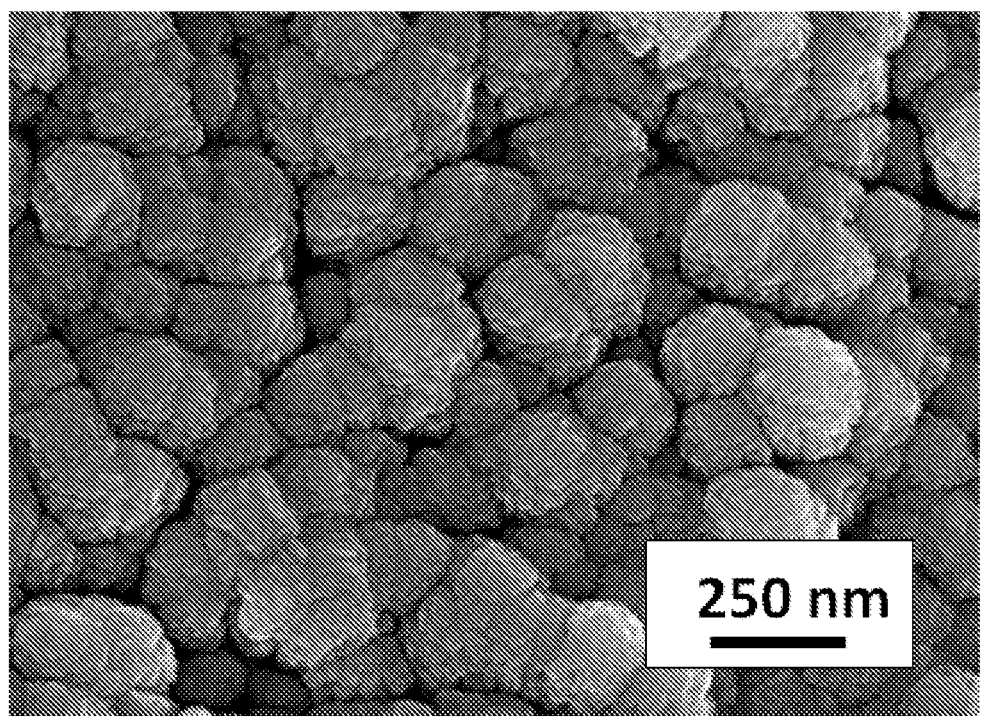
FIG. 2d is a 250 k× SEM micrograph of the surface of a $(Ir_{1-x}Rh_x)_nO_{n+y}$ thin film according to the invention wherein x is 0.54, n is 1 and y is 1 prepared by reactive sputtering at 80% oxygen partial pressure.

Importantly, the films have a stable surface structure which does not contain "platelets", like the surface of IrO₂ shown in FIG. 1b. This can be seen in the SEM images in FIGS. 2c and 2d which were acquired using the same equipment described above for the IrO₂ films. FIG. 2c shows the surface of a $(Ir_{0.25}Rh_{0.75})_{1.5}O_{2.5}$ thin film sputtered at 20% oxygen partial pressure and FIG. 2d shows the surface of a $(Ir_{0.46}Rh_{0.54})O_2$ thin film sputtered at 80% oxygen partial pressure. These surfaces would be stable in the biological environment.

The stoichiometries (as well as atomic arrangement (i.e. crystal structure)) were identified from XRD patterns and verified by energy dispersive spectroscopy. FIG. 2b provides an illustration of XRD spectra obtained from thin film coatings according to the invention. Provided is a set of XRD spectra for five thin film coatings $(Ir_{1-x}Rh_x)_nO_{n+1}$ prepared by reactive sputtering at 80% oxygen partial pressure. The percentages of Ir, Rh and oxygen are provided by each spectra. The peaks labelled "ss" are from the stainless steel substrate. Those labelled with numbers, such as 110, are x-ray diffraction peaks from atomic planes labelled by their Miller indices within the tetragonal crystal structure.

Experimental Procedure

Thin films were deposited in accordance with GEP 2 using elemental Ir and Rh cathode targets.

For investigation of the role of oxygen partial pressure, the relative Ar and $O_2$ flow rates were adjusted. The sum of the flow rates was held at a constant flow of 50 sccm, but the individual mass-flow controllers were varied to adjust the content of $O_2$ to 20%, 50% and 80% $O_2$ partial pressure (FIG. 2a). The coating thickness for these samples was 150-480 nm, with the sum of the cathode powers again held constant at 100 W. FIGS. 2c and 2d were sputtered at 20 and 80% oxygen partial pressure respectively.

Oxide Films Containing Ir and Ru

Results

Oxide films containing Ir and Ru were prepared at various thicknesses, and with varying Ir and Ru content, by reactive sputtering using Ar and at 20%, 50% and 80% $O_2$ partial pressures and measured for CSC. The results are shown in FIG. 3a.

Figure 3A:
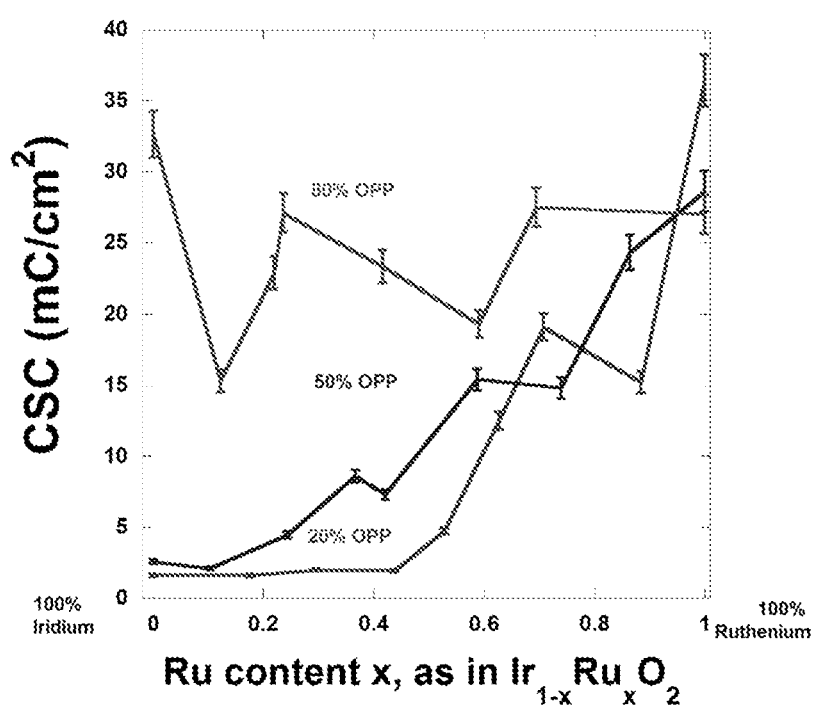
FIG. 3a is a chart showing charge storage capacities for thin film coatings $(Ir_{1-x}Ru_x)O_2$ according to the invention at various atomic percentages of Ir and Ru, prepared by reactive sputtering at 20, 50 and 80% oxygen partial pressure.

As shown in FIG. 3a, the CSC of oxide films containing Ir and Rh can be significantly increased by increasing the $O_2$ partial pressure used to synthesize the films, as well as controlling the atomic ratio of Ir to Ru in the material.

Figure 3B:
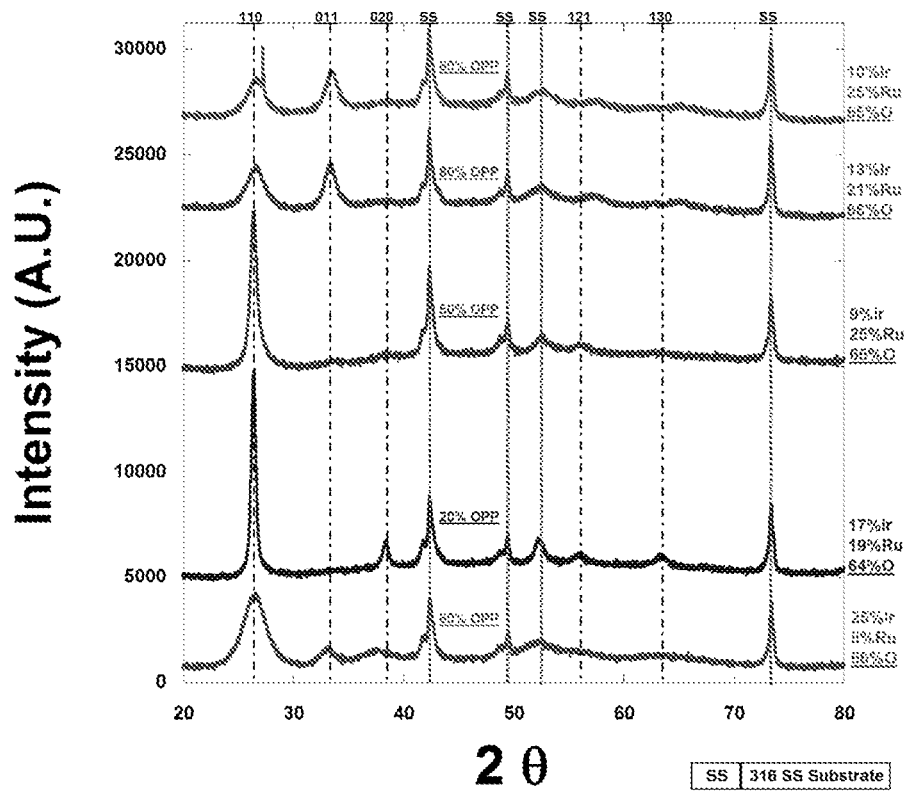
FIG. 3b shows a set of XRD spectra for five thin film coatings $(Ir_{1-x}Ru_x)_nO_{n+y}$ prepared by reactive sputtering at 20, 50 and 80% oxygen partial pressure. The percentages of Ir, Ru and oxygen, and sputtering oxygen partial pressure, for each thin film coating are shown in the figure.
Figure 3C:
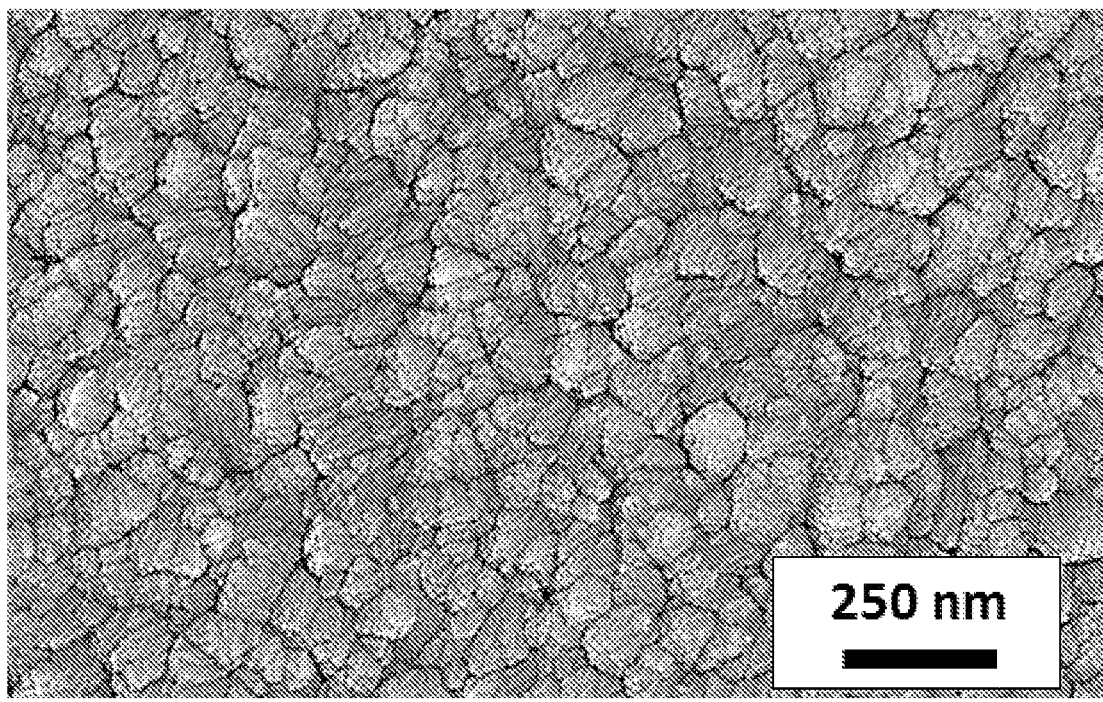
FIG. 3c is a 250 k× SEM micrograph of the surface of an $(Ir_{1-x}Ru_x)_nO_{n+1}$ thin film according to the invention wherein x is 0.74 and n is 1 sputtered at 80% oxygen partial pressure.

Importantly, the films have a stable surface structure which does not contain "platelets", like the surface of $IrO_2$ shown in FIG. 1b. This can be seen in the SEM images in FIG. 3c which were acquired using the same equipment described above for the $IrO_2$ films. FIG. 3c shows the surface of a $(Ir_{1-x}Rh_x)_nO_{n+1}$ thin film sputtered at 80% $O_2$ partial pressure. This surface would be stable in the biological environment.

The stoichiometries (as well as atomic arrangement (i.e. crystal structure)) were identified from XRD patterns and verified by energy dispersive spectroscopy. FIG. 3b provides an illustration of XRD spectra obtained from thin film coatings according to the invention. Provided is a set of XRD spectra for five thin film coatings $(Ir_{1-x}Ru_x)_nO_{n+1}$ prepared by reactive sputtering at 20, 50 and 80% oxygen partial pressure (as shown in the figure) in which the percentages of Ir, Ru and oxygen are provided by each spectra. The peaks in the patterns correspond to a tetragonal crystal structure with multiple orientation (110, 011, 121 etc) and a stoichiometry of $(IrRu)O_2$.

Experimental Procedure

Thin films were deposited in accordance with GEP 2 using elemental Ir and Ru cathode targets.

For investigation of the role of oxygen partial pressure, the relative Ar and $O_2$ flow rates were adjusted. The sum of the flow rates was held at a constant flow of 50 sccm, but the individual mass-flow controllers were varied to adjust the content of $O_2$ to 20%, 50% and 80% $O_2$ partial pressure (FIG. 3a). The target thickness for these samples was 150-400 nm. The cathode power was again held constant at 100 W. FIG. 3c was sputtered at 80% $O_2$ partial pressure.

Oxide Films Containing Ir and Rh and Ru

Results

Oxide films containing Ir, Rh and Ru were prepared at a thickness of 200-500 nm, and with varying Ir, Rh and Ru content, by reactive sputtering using Ar at 20% $O_2$ partial pressure and measured for CSC. The results are shown in FIG. 6a. The left hand diagram in FIG. 6a is a diagram with points showing the compositions of various thin film materials prepared. The right hand diagram is a heat map showing what compositions give the highest CSC values. There is also an indication of what the surface structure is in the areas of the heat map with highest CSC. The nanocrystalline microstructure is preferred because the nanoflake microstructure is likely to be unstable in medical device operating conditions. FIG. 6b is an SEM image of the surface of a preferred thin film containing 21.51% Ir, 10.52% Rh, 2.89% Ru and 64.99% O. The surface has a suitable microstructure. The stoichiometries (as well as atomic arrangement (i.e. crystal structure)) were identified from XRD patterns and verified by energy dispersive spectroscopy.

FIG. 6c is an SEM image of the surface of a preferred thin film containing 24.5% Ir, 8.6% Rh, 1.4% Ru and 65.5% O. The surface has a suitable microstructure and is high performing in terms of CSC. The figure illustrates grains used to identify average aspect ratio and average circularity. On this surface the average aspect ratio is 0.795±0.141 and the average circularity is 0.592±0.059.

Experimental Procedure

Thin films were deposited on 316 stainless steel at room temperature. Six-inch diameter substrates which covered the entire area of the sample holder were adhered with double sided copper tape so they would remain stationary when inserted through the load lock into the deposition chamber allowing them to be coated in a single deposition.

The sputtering chamber was evacuated to a base pressure of $<2\times10^{-7}$ Torr with a Leybold 1000C turbo-pump backed by an Alcatel Drytel 34 dry pump. 50.8 mm diameter, 3.175 mm thick elemental metal targets were used as the cathode with a working distance of approximately 75 mm. A pulsed-DC power supply (Advanced Energy Pinnacle Plus) with a frequency of 140 kHz, and a reverse period of 1 µs was used as the sputtering source (~42% duty cycle) for the Ir target, a second pulsed DC power supply (Kurt J Lesker Company TruPlasma) operated in DC mode and a DC power supply (MDX-1000) were used for the other metal(s) target. The sum of the powers between both types of power supply were held constant at 100 W±1 (Pulsed DC+DC=100 W) and the amount of power supplied to each cathode was held at 33 W±1. This resulted in an average of 425 V (60 V reverse bias) and 0.08 A on the target at a deposition pressure of 30 mTorr. With a total flow rate of Ar and $O_2$ at 50 sccm, the "downstream" pressure-controlling baffle valve that throttled the pumping effectiveness was at a position of approximately 20% open.

The coatings were synthesized by combinatorial sputtering from elemental metal targets in an $O_2$/Ar gas mixture (or as otherwise specified). The sample holder remained stationary during deposition allowing for the atomic ratio of metals to vary based on the substrate location with respect to each elemental target/cathode. With a total flow rate of Ar and O$_2$ at 50 sccm, the "downstream" pressure controlling baffle valve that throttled the pumping effectiveness was at a position of approximately 20% open. The substrates were etched using an RF-power supply running at 100 W for 5 minutes prior to deposition to improve adhesion. Each cathode was pre-sputtered for 5 minutes at 50 W with an Ar flowrate of 50 sccm to remove any layers of oxidation that may have formed on the surface of the target to better control deposition rates and coating composition.

The deposition temperature was controlled using a resistive heater machined from a thin molybdenum sheet. A K-type thermocouple was used as the temperature sensor. The sensor was positioned below the heater in a ceramic block. Its specific placement was determined so that its measured temperature matched the temperature measured on the surface of the stainless-steel substrate tray (above the heater) using a pyrometer (LAND CYCLOPS 153A). The positioning was performed at a temperature of 500° C.—the minimum temperature where the pyrometer was effective. The temperature was controlled by connecting the thermocouple to a Honeywell DCP 216 temperature controller.

Oxide Films Containing Ir and Pd

Results

Oxide films containing Ir and Pd were prepared at various thicknesses, and with varying Ir and Pd content, by reactive sputtering using Ar and at 20%, 50% and 80% O$_2$ partial pressures and measured for CSC. The results are shown in FIG. 7a.

Figure 7A:
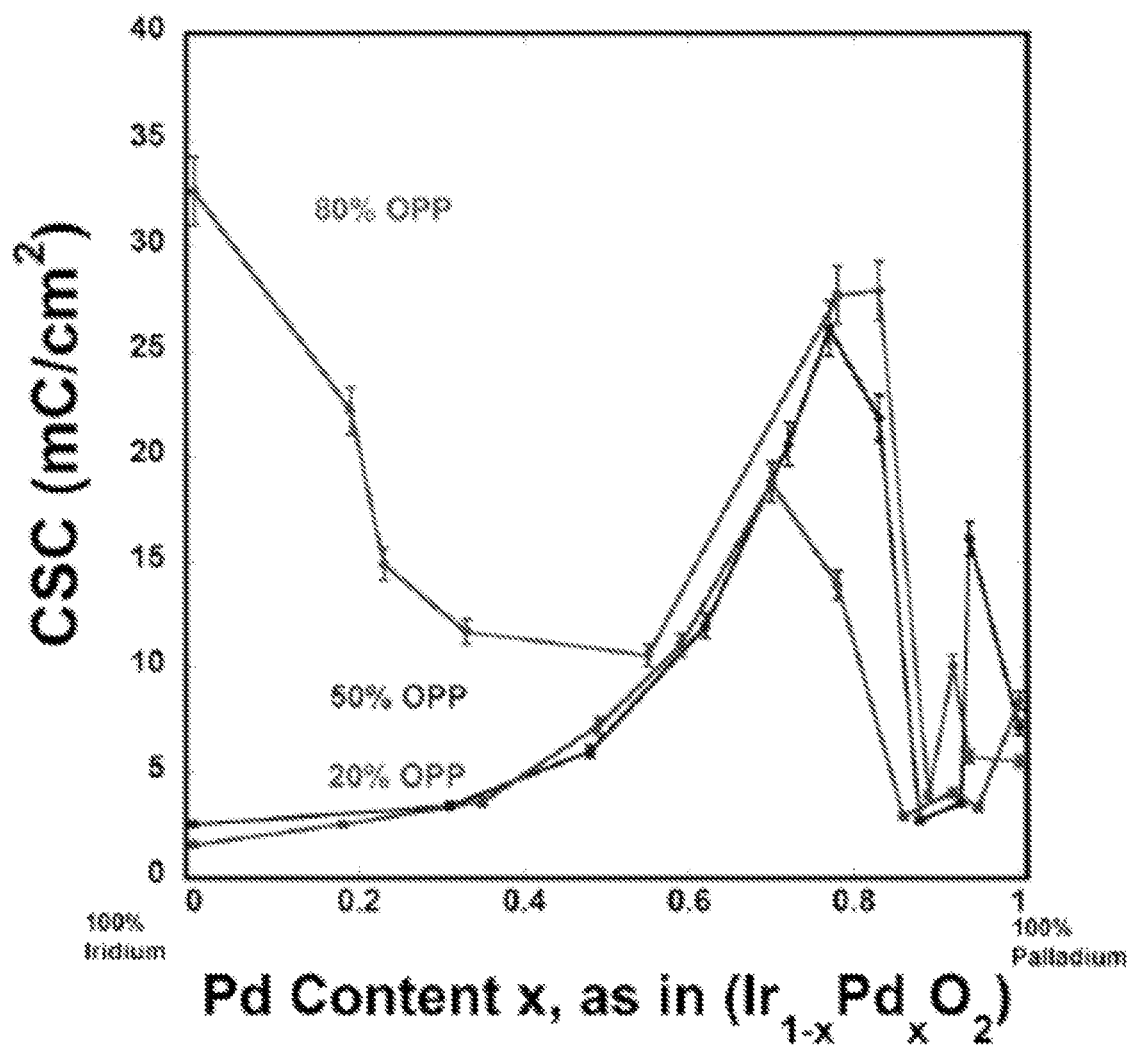
FIG. 7a is a chart showing charge storage capacities for thin film coatings $(Ir_{1-x}Pd_x)O_2$ according to the invention at various atomic percentages of Ir and Pd, prepared by reactive sputtering at 20, 50 and 80% oxygen partial pressure.

As shown in FIG. 7a, the CSC of oxide films containing Ir and Pd can be significantly increased by controlling the O$_2$ partial pressure used to synthesize the films, as well as controlling the atomic ratio of Ir to Pd in the material.

Figure 7B:
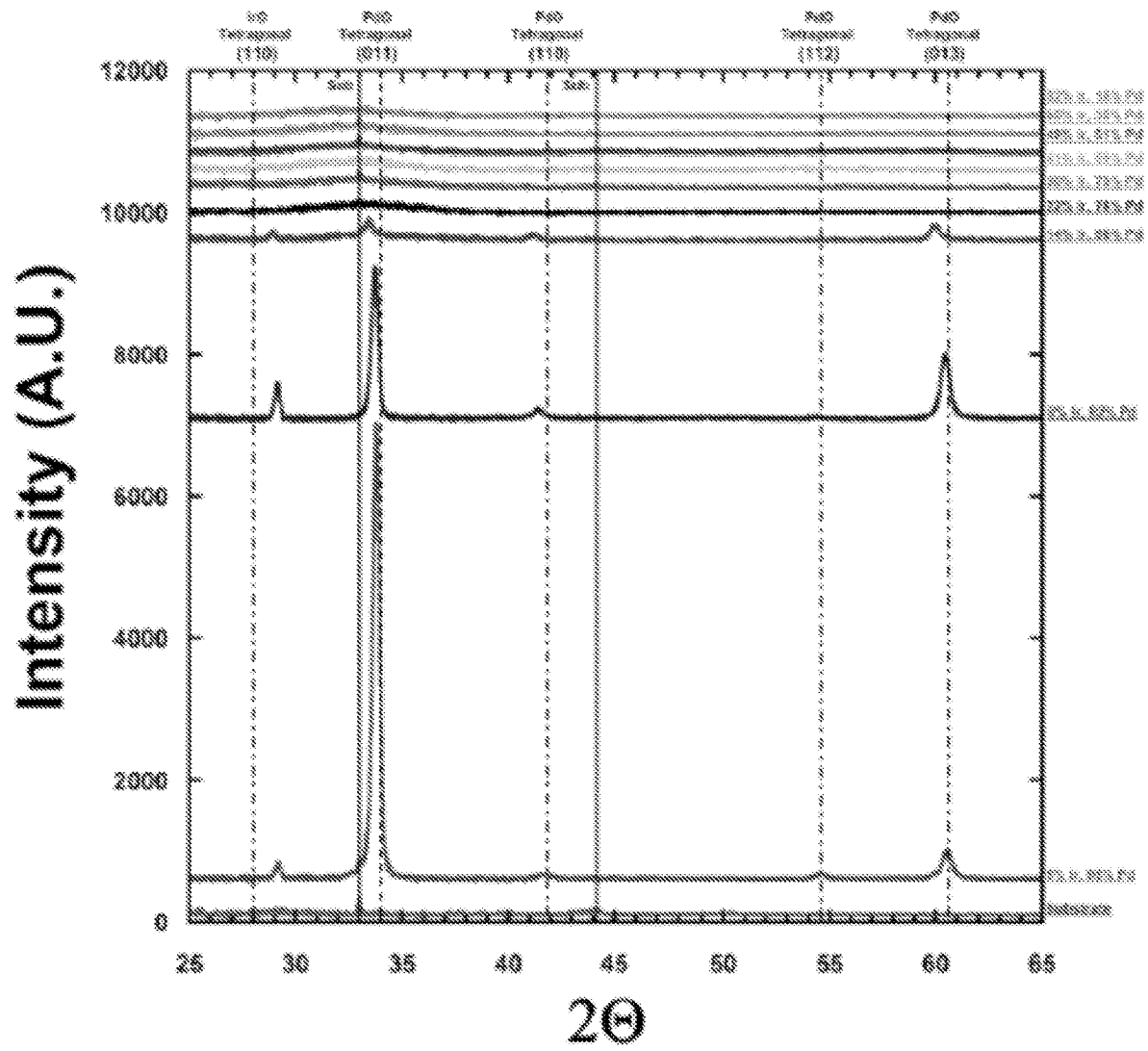
FIG. 7b shows a set of XRD spectra for nine thin film coatings $(Ir_{1-x}Pd_x)_nO_2$ prepared by reactive sputtering at 20% oxygen partial pressure. The percentages of Ir, Pd and oxygen are provided by each spectra.
Figure 7C:
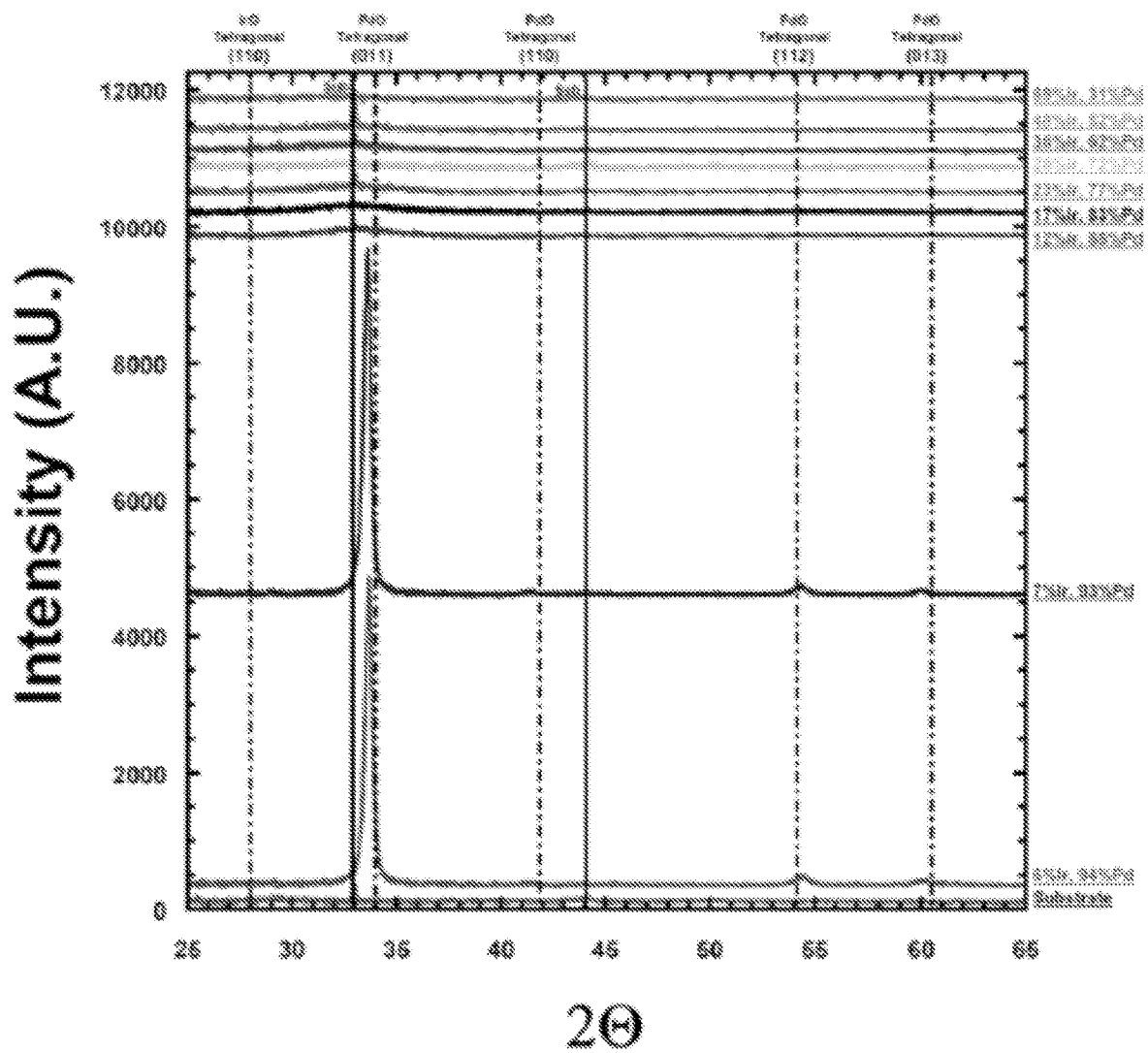
FIG. 7c shows a set of XRD spectra for nine thin film coatings $(Ir_{1-x}Pd_x)_nO_2$ prepared by reactive sputtering at 50% oxygen partial pressure. The percentages of Ir, Pd and oxygen are provided by each spectra.
Figure 7D:
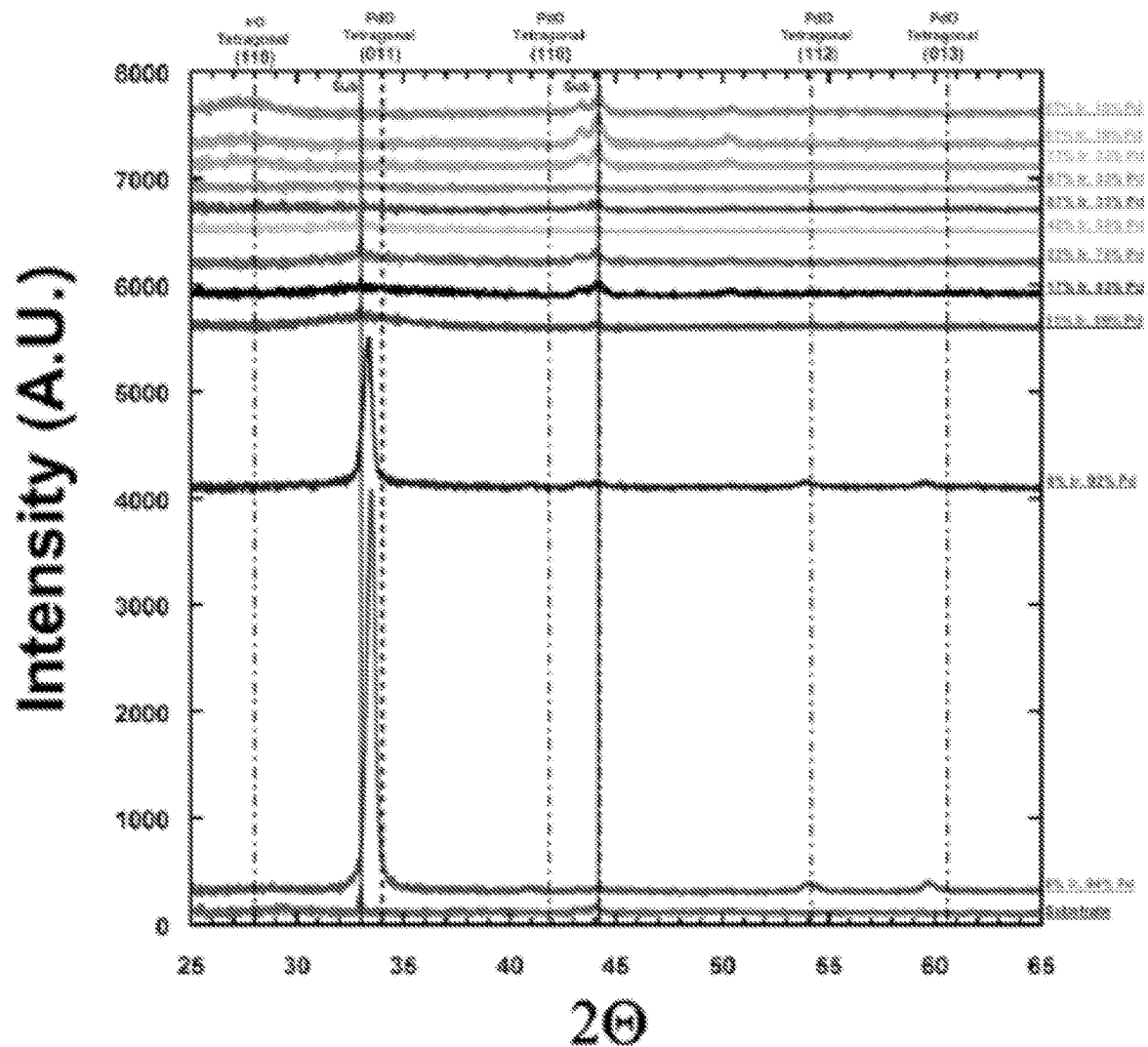
FIG. 7d shows a set of XRD spectra for eleven thin film coatings $(Ir_{1-x}Pd_x)_nO_2$ prepared by reactive sputtering at 80% oxygen partial pressure. The percentages of Ir, Pd and oxygen are provided by each spectra.
Figure 7E:
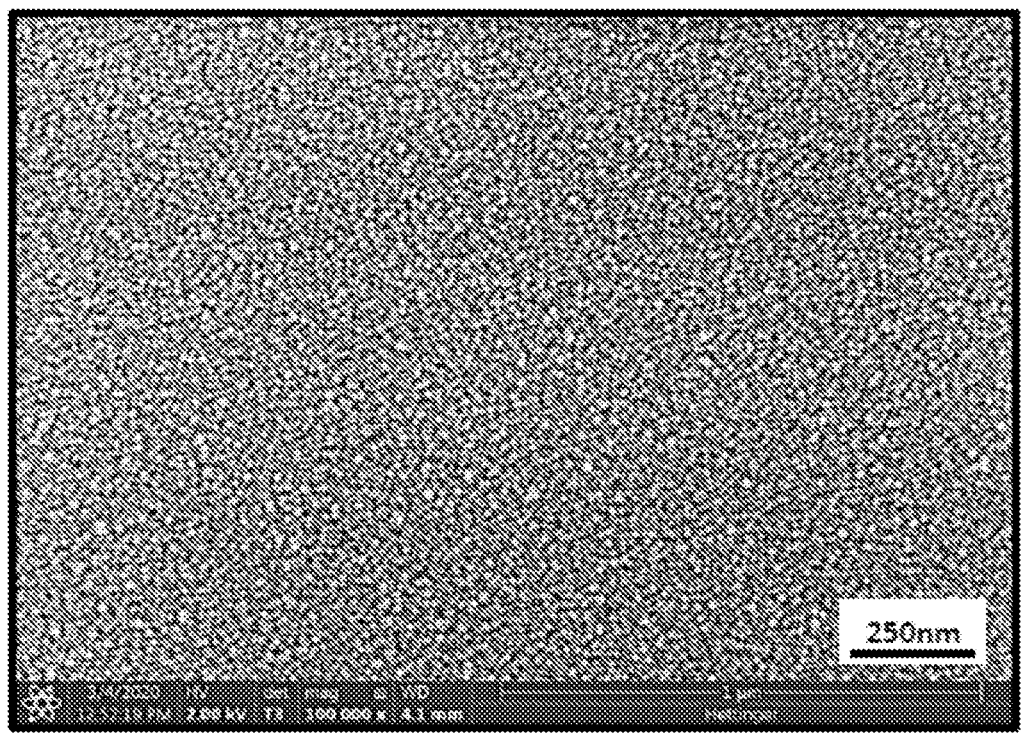
FIG. 7e is a 250 k× SEM micrograph of the surface of a $(Ir_{1-x}Pd_x)_nO_{n+y}$ thin film according to the invention wherein x is 0.72, n is 1 and y is 1 prepared by reactive sputtering at 50% oxygen partial pressure.

Importantly, the films have a stable surface structure which does not contain "platelets", like the surface of IrO$_2$ shown in FIG. 1b. This can be seen in the SEM image in FIG. 7e which was acquired using the same equipment described above for the IrO$_2$ films. FIG. 7e shows the surface of a $(Ir_{1-x}Pd_x)_nO_{n+y}$ thin film according to the invention wherein x is 0.72, n is 1 and y is 1 prepared by reactive sputtering at 50% oxygen partial pressure.

The stoichiometries (as well as atomic arrangement (i.e. crystal structure)) were identified from XRD patterns and verified by energy dispersive spectroscopy. FIGS. 7b, c and d provide illustrations of XRD spectra obtained from thin film coatings according to the invention. Provided are sets of XRD spectra for nine thin film coatings $(Ir_{1-x}Pd_x)_nO_{n+1}$ (different nine in each figure) prepared by reactive sputtering at 20, 50 and 80% oxygen partial pressure (as shown in the figure) in which the percentages of Ir, Pd and oxygen are provided by each spectra.

Experimental Procedure

Thin films were deposited in accordance with GEP 2 using elemental Ir and Pd cathode targets.

For investigation of the role of oxygen partial pressure, the relative Ar and O$_2$ flow rates were adjusted. The sum of the flow rates was held at a constant flow of 50 sccm, but the individual mass-flow controllers were varied to adjust the content of O$_2$ to 20%, 50% and 80% O$_2$ partial pressure (FIG. 7a). The target thickness for these samples was 150-400 nm. The cathode power was again held constant at 100 W.

Rh$_{a-1}$O$_a$ Films

Results

Rh$_{a-1}$O$_a$ films were prepared by reactive sputtering using Ar and at 5%, 10%, 20%, 30%, 40%, 50%, 60%, 70%, 80% and 90% O$_2$ partial pressure and measured for CSC. The results are shown in FIG. 4a.

Figure 4A:
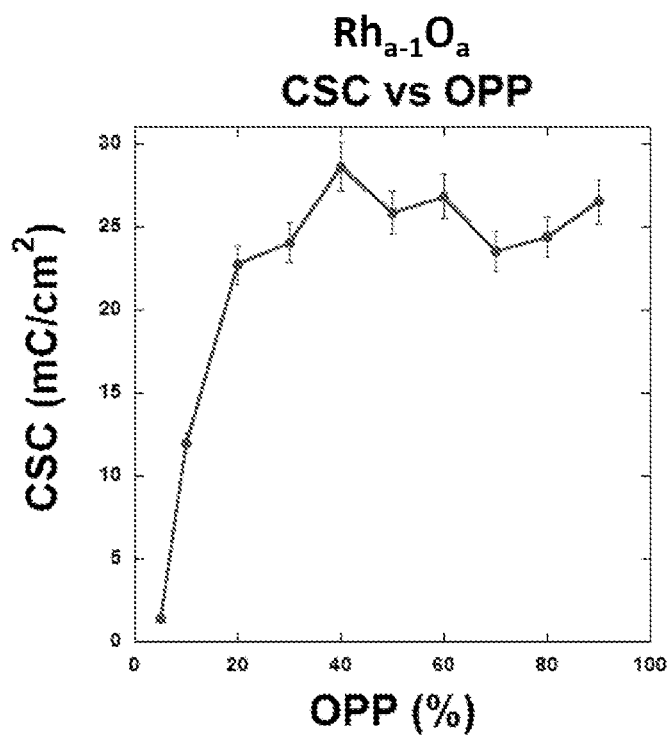
FIG. 4a is a chart showing charge storage capacities for thin film coatings of $Rh_{a-1}O_a$ according to the invention prepared by reactive sputtering at a variety of oxygen partial pressures.
Figure 4B:
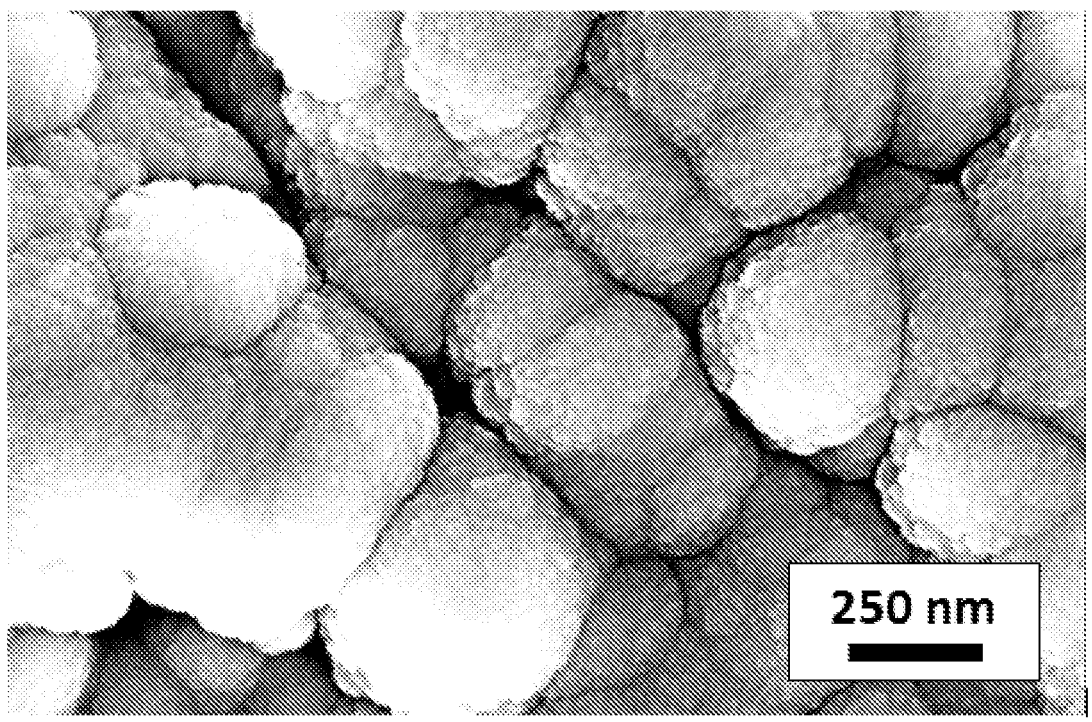
FIG. 4b is a 250 k× SEM micrograph of the surface of a $Rh_2O_3$ thin film according to the invention sputtered at 20% oxygen partial pressure.
Figure 4C:
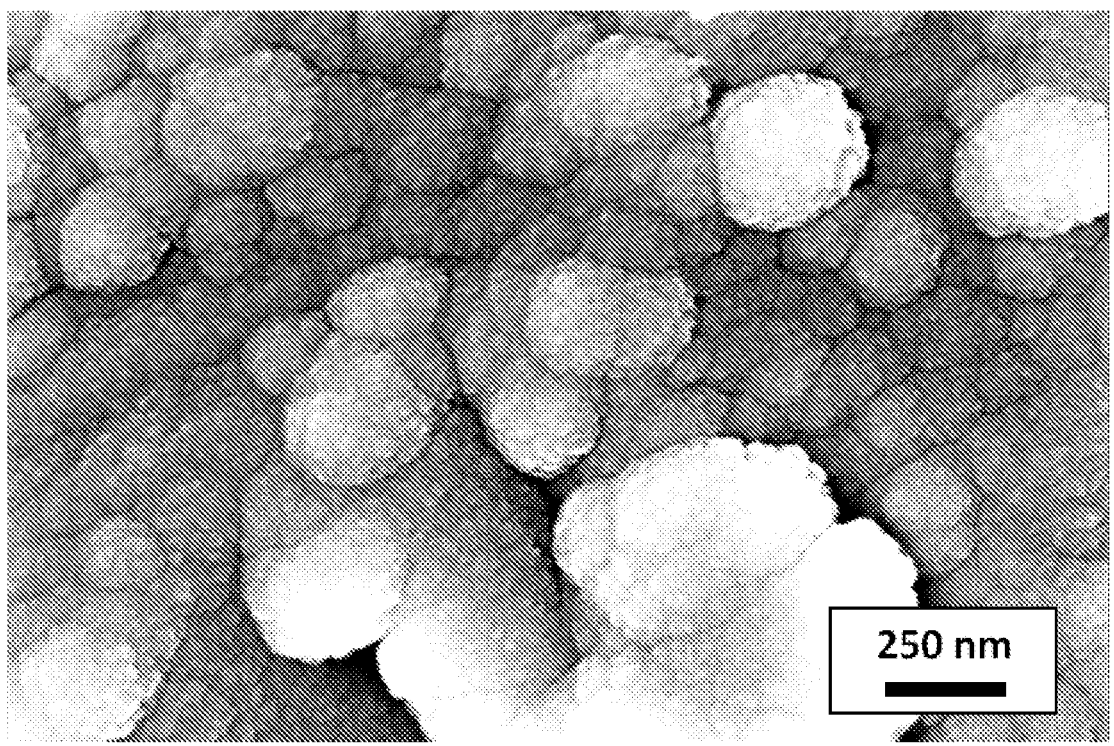
FIG. 4c is a 250 k× SEM micrograph of the surface of a $Rh_2O_3$ thin film according to the invention sputtered at 50% oxygen partial pressure.
Figure 4D:
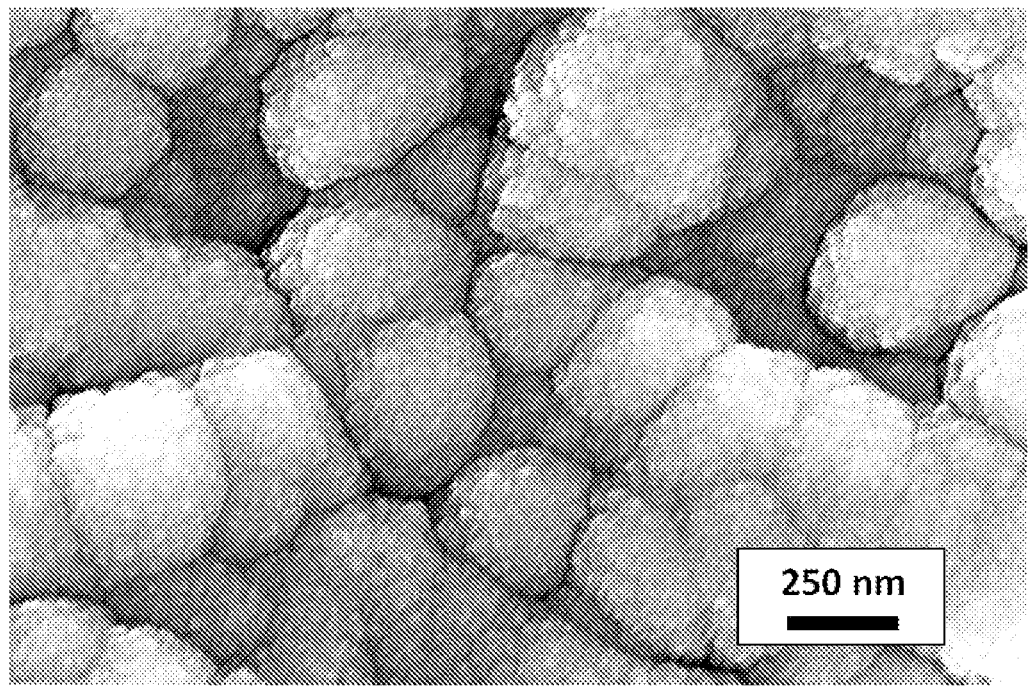
FIG. 4d is a 250 k× SEM micrograph of the surface of a $RhO_2$ thin film according to the invention sputtered at 80% oxygen partial pressure.

As shown in FIG. 4a, the CSC of Rh$_2$O$_3$ increases with an increase in O$_2$ partial pressure used during sputtering. Importantly, the films have a stable surface structure which does not contain "platelets", like the surface of IrO$_2$ shown in FIG. 1b. This can be seen in the SEM image in FIGS. 4b-d which were acquired using the same equipment described above for the IrO$_2$ films. FIG. 4b shows a Rh$_2$O$_3$ thin film sputtered at 20% oxygen partial pressure. FIG. 4c shows a RhO$_2$ thin film sputtered at 50% oxygen partial pressure. FIG. 4d shows a RhO$_2$ thin film sputtered at 80% oxygen partial pressure. These surfaces would be stable in the biological environment.

Experimental Procedure

Thin films were deposited in accordance with GEP 1 with an elemental Rh cathode target.

For investigation of the role of oxygen partial pressure, the relative Ar and O$_2$ flow rates were adjusted. The sum of the flow rates was held at a constant flow of 50 sccm, but the individual mass-flow controllers were varied to adjust the content of O$_2$ to 5, 10, 20, 30, 40, 50, 60, 70 and 90% oxygen partial pressure (as shown in FIG. 4a). The thickness of the films in FIG. 4a were in the range of 130-500 nm, FIG. 4b 440 nm, FIG. 4c 250 nm, FIG. 4d 150 nm. The cathode power was again held constant at 100 W.

RuO$_b$ Films

Results

RuO$_b$ films were prepared by reactive sputtering using Ar and at 5%, 10%, 20%, 30%, 40%, 50%, 60%, 70%, 80% and 90% O$_2$ partial pressure and measured for CSC. The results are shown in FIG. 5a.

Figure 5A:
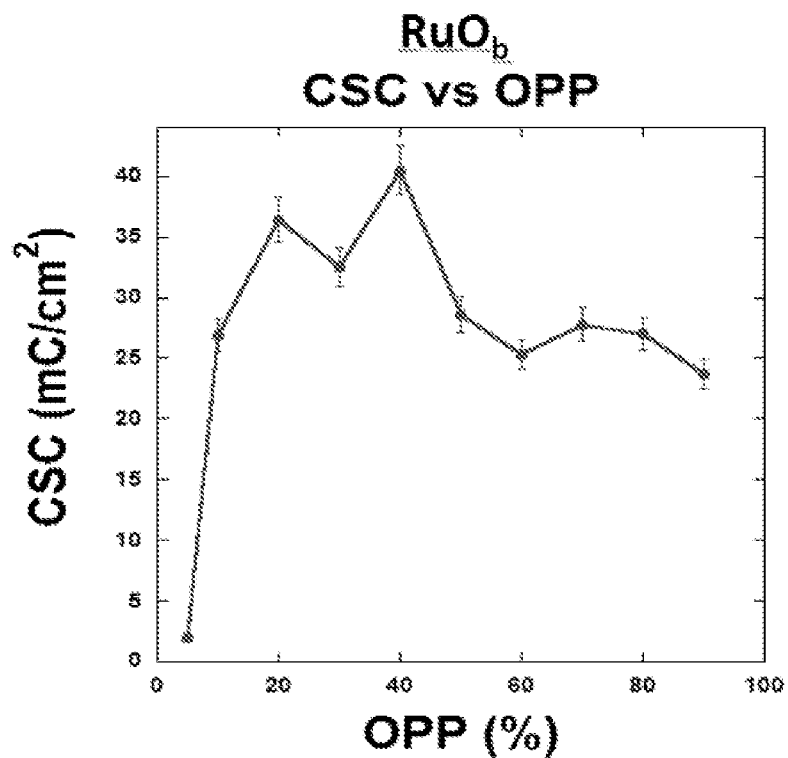
FIG. 5a is a chart showing charge storage capacities for thin film coatings of $RuO_b$ according to the invention prepared by reactive sputtering at a variety of oxygen partial pressures.
Figure 5B:
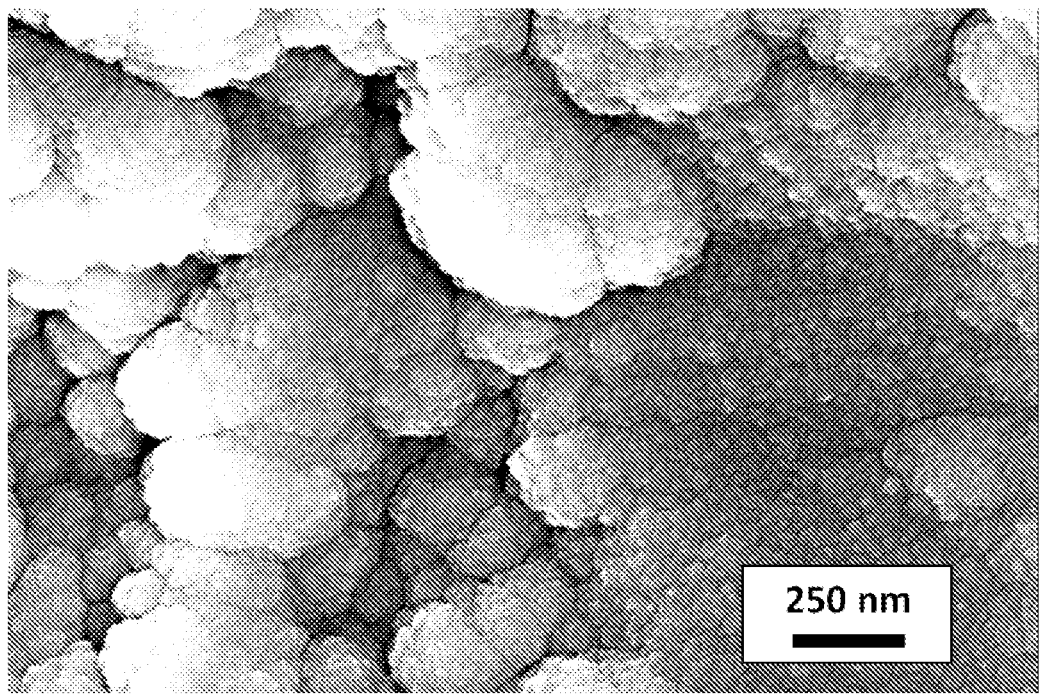
FIG. 5b is a 250 k× SEM micrograph of the surface of a $RuO_2$ thin film according to the invention sputtered at 20% oxygen partial pressure.
Figure 5C:
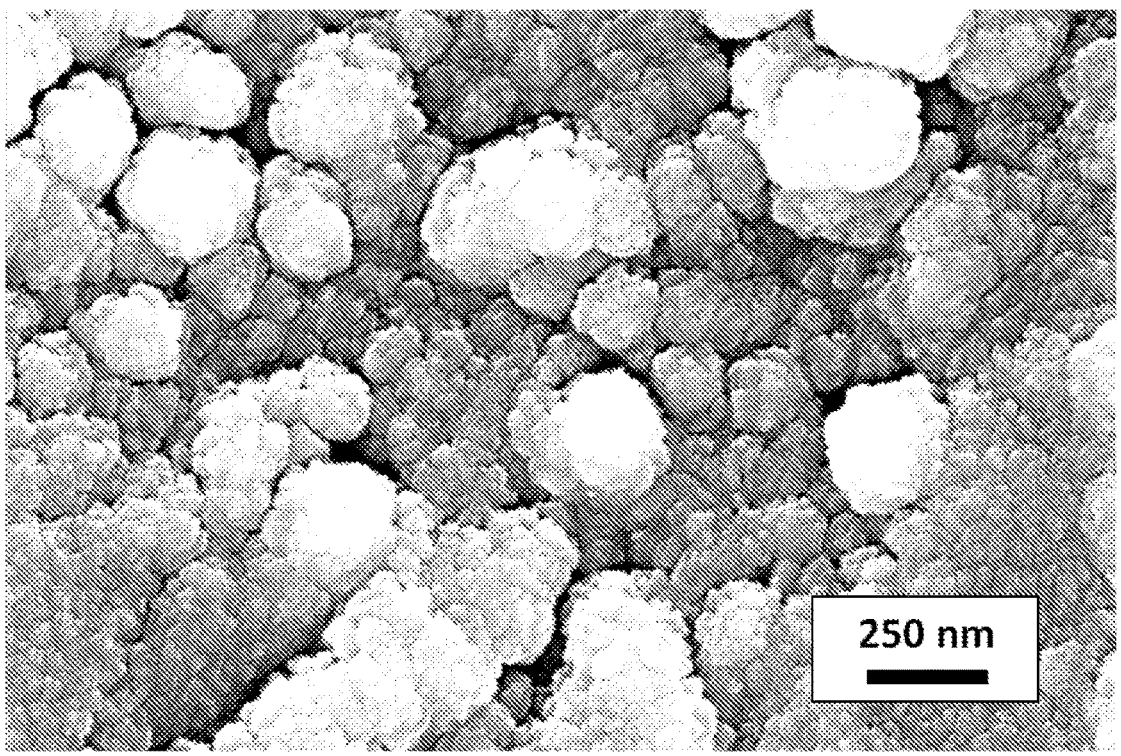
FIG. 5c is a 250 k× SEM micrograph of the surface of a $RuO_2$ thin film according to the invention sputtered at 50% oxygen partial pressure.
Figure 5D:
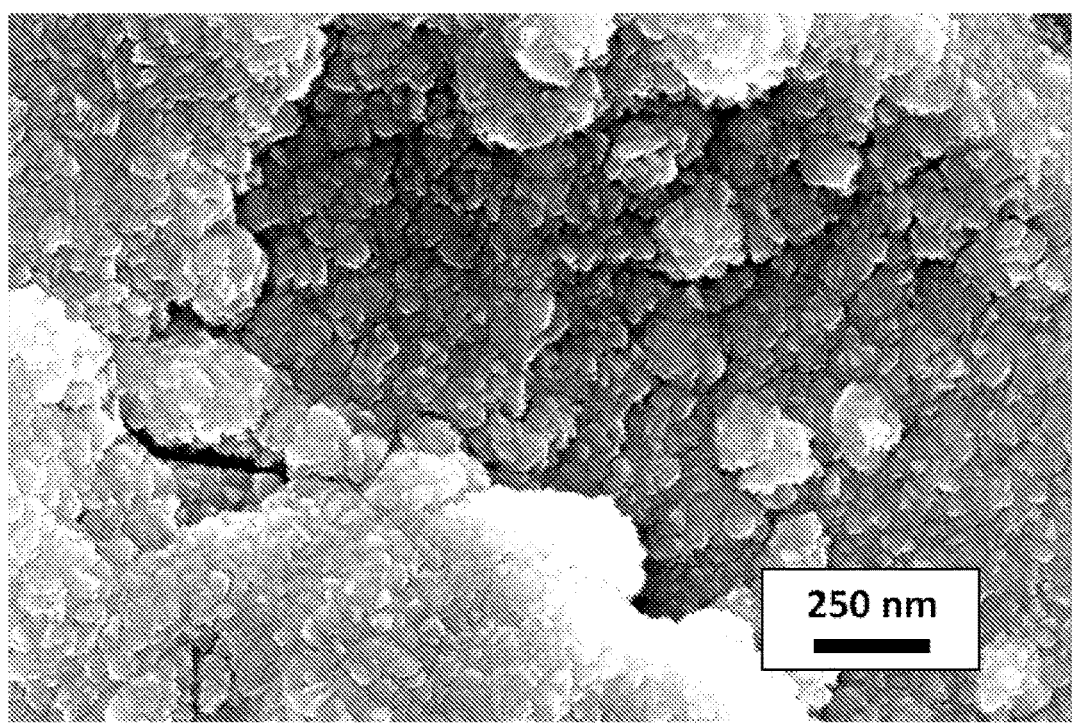
FIG. 5d is a 250 k× SEM micrograph of the surface of a $RuO_4$ thin film according to the invention sputtered at 80% oxygen partial pressure.

As shown in FIG. 5a, the CSC of RuO$_2$ generally increases with an increase in O$_2$ partial pressure used during sputtering. Importantly, the films have a stable surface structure which does not contain "platelets", like the surface of IrO$_2$ shown in FIG. 1b. This can be seen in the SEM image in FIGS. 5b-d which were acquired using the same equipment described above for the IrO$_2$ films. FIG. 5b shows a RuO$_2$ thin film sputtered at 20% oxygen partial pressure. FIG. 5c shows a RuO$_2$ thin film sputtered at 50% oxygen partial pressure. FIG. 5d shows a RuO$_4$ thin film sputtered at 80% oxygen partial pressure. These surfaces would be stable in the biological environment.

Experimental Procedure

Thin films were deposited in accordance with GEP 1 with an elemental Ru cathode target.

For investigation of the role of oxygen partial pressure, the relative Ar and O$_2$ flow rates were adjusted. The sum of the flow rates was held at a constant flow of 50 sccm, but the individual mass-flow controllers were varied to adjust the content of O$_2$ to 5, 10, 20, 30, 40, 50, 60, 70 and 90% oxygen partial pressure (as shown in FIG. 5a). The thickness of the films in FIG. 5a were in the range of 80 to 460 nm, FIG. 5b 400 nm, FIG. 5c 275 nm, FIG. 5d 150 nm. The cathode power was again held constant at 100 W.

REFERENCES

[1] A. R. Harris, A. G. Paolini, G. G. Wallace, Effective Area and Charge Density of Iridium Oxide Neural Electrodes, Electrochimica Acta, 230 (2017) 285-292.

[2] S. Thanawala, D. G. Georgiev, R. J. Baird, G. Auner, Characterization of iridium oxide thin films deposited by pulsed-direct-current reactive sputtering, Thin Solid Films, 515 (2007) 7059-7065.

[3] I. G. Casella, M. Contursi, R. Toniolo, Anodic electrodeposition of iridium oxide particles on glassy carbon surfaces and their electrochemical/SEM/XPS characterization, Journal of Electroanalytical Chemistry, 736 (2015) 147-152.

[4] P.-C. Chen, Y.-C. Chen, C.-N. Huang, Free-standing iridium oxide nanotube array for neural interface electrode applications, Materials Letters, 221 (2018) 293-295.

[5] S. Negi, R. Bhandari, L. Rieth, F. Solzbacher, Effect of sputtering pressure on pulsed-DC sputtered iridium oxide films, Sensors and Actuators B: Chemical, 137 (2009) 370-378.

[6] H. J. Cho, H. Horii, C. S. Hwang, J. W. Kim, C. S. Kang, B. T. Lee, S. I. Lee, Y. B. Koh, M. Y. Lee, Preparation and characterization of iridium oxide thin films grown by DC reactive sputtering, Jpn J Appl Phys 1, 36 (1997) 1722-1727.

[7] Cogan, Stuart F. "Neural Stimulation and Recording Electrodes." *Annual Review of Biomedical Engineering*, vol. 10, no. 1, 2008, pp. 275-309.

[8] Kang, Xiao-Yang, et al. "Fabrication and Electrochemical Comparison of SIROF-AIROF-EIROF Microelectrodes for Neural Interfaces." 2014 *36th Annual International Conference of the IEEE Engineering in Medicine and Biology Society*, 2014.

The invention claimed is:

1. A medical device comprising an electrode, the electrode comprising a thin film coating comprising a metal oxide material, wherein the metal oxide material has the formula $(Ir_{1-x}[MM']_x)_nO_{n+y}$, wherein;
   x is in the range of and including 0.05 to less than 1;
   n is in the range of and including 1 to 2;
   y is in the range of and including 0 to 3;
   M and M' are different and are respectively Ru, Rh, Pd, Os or Pt; and
   wherein the thin film coating has a thickness in the range of and including 100 to 2000 nm.

2. The medical device according to claim 1, wherein n+y does not exceed 4.

3. The medical device according to claim 1, wherein x is in the range of and including 0.05 to 0.95.

4. The medical device according to claim 1, wherein M and M' are each independently Ru, Rh or Pd.

5. The medical device according to claim 1, wherein M and M' are each independently Ru or Rh.

6. The medical device according to claim 1, wherein M is Ru and M' is Rh.

7. The medical device according to claim 1, wherein the thin film coating has a charge storage capacity of at least 5 $mC/cm^2$.

8. The medical device according to claim 7, wherein the thin film coating has a charge storage capacity of at least 25 $mC/cm^2$.

9. The medical device according to claim 1, wherein the surface of the thin film coating consists of grains having an average aspect ratio in the range of and including 0.25 to 1, and an average circularity in the range of and including 0.25 to 1.

10. The medical device according to claim 1, wherein the medical device is biologically implantable.

11. The medical device according to claim 10, wherein the medical device is a cortical visual prosthesis, prosthetic limb, sacral nerve stimulator, spinal cord stimulator, gastric electric stimulator, deep brain stimulator, valgus nerve stimulator, electrophysiology catheter, cochlear implant, neurostimulator or a cardiac rhythm management device.

12. The medical device according to claim 1, wherein the medical device is diagnostic.

13. An electrode comprising a thin film coating, the thin film coating comprising a metal oxide material, wherein the metal oxide material has the formula $(Ir_{1-x}[MM']_x)_nO_{n+y}$, wherein;
   x is in the range of and including 0.05 to less than 1;
   n is in the range of and including 1 to 2;
   y is in the range of and including 0 to 3;
   M and M' are different and are respectively Ru, Rh, Pd, Os or Pt; and
   wherein the thin film coating has a thickness in the range of and including 100 to 2000 nm.

14. A method of making an electrode comprising providing a thin film coating on a substrate, the thin film coating comprising a metal oxide material, wherein the metal oxide material has the formula $(Ir_{1-x}[MM']_x)_nO_{n+y}$, wherein;
   x is in the range of and including 0.05 to less than 1;
   n is in the range of and including 1 to 2;
   y is in the range of and including 0 to 3;
   M and M' are different and are respectively Ru, Rh, Pd, Os or Pt; and
   wherein the thin film coating has a thickness in the range of and including 100 to 2000 nm.

* * * * *